(12) United States Patent
Duan et al.

(10) Patent No.: US 12,291,729 B2
(45) Date of Patent: May 6, 2025

(54) ENGINEERED CAS PROTEIN AND USE THEREOF

(71) Applicant: SHANDONG SHUNFENG BIOTECHNOLOGY CO.LTD., Jinan (CN)

(72) Inventors: Zhiqiang Duan, Jinan (CN); Ying Chen, Jinan (CN); Fengming Han, Jinan (CN)

(73) Assignee: SHANDONG SHUNFENG BIOTECHNOLOGY CO.LTD., Jinan (CN)

( * ) Notice: Subject to any disclaimer, the term of this patent is extended or adjusted under 35 U.S.C. 154(b) by 0 days.

(21) Appl. No.: 18/406,232

(22) Filed: Jan. 8, 2024

(65) Prior Publication Data
US 2025/0011739 A1  Jan. 9, 2025

Related U.S. Application Data

(63) Continuation of application No. PCT/CN2023/134558, filed on Nov. 28, 2023.

(30) Foreign Application Priority Data

| Jul. 7, 2023 | (CN) | 202310830438.1 |
| Aug. 1, 2023 | (CN) | 202310961664.3 |
| Aug. 25, 2023 | (CN) | 202311078840.5 |
| Sep. 22, 2023 | (CN) | 202311230471.7 |

(51) Int. Cl.
| C12N 15/00 | (2006.01) |
| C12N 9/22 | (2006.01) |
| C12N 15/10 | (2006.01) |
| C12N 15/11 | (2006.01) |
| C12N 15/63 | (2006.01) |

(52) U.S. Cl.
CPC .............. *C12N 9/22* (2013.01); *C12N 15/102* (2013.01); *C12N 15/111* (2013.01); *C12N 15/63* (2013.01); *C12N 2310/20* (2017.05)

(58) Field of Classification Search
CPC ................. C12N 15/62; C12N 2310/20; C07K 2319/00; C07K 2319/80
See application file for complete search history.

(56) References Cited

U.S. PATENT DOCUMENTS

| 10,266,851 B2* | 4/2019 | Chen ............... C12N 9/22 |
| 2016/0177278 A1* | 6/2016 | Wolfe .............. C12N 9/22 435/199 |
| 2021/0395784 A1* | 12/2021 | Lai ................ C12N 15/902 |
| 2022/0195405 A1* | 6/2022 | Garvey ............ C12N 9/22 |

FOREIGN PATENT DOCUMENTS

| CN | 109207477 A | 1/2019 |
| CN | 111770992 B | 4/2021 |
| CN | 111757889 B | 5/2021 |
| CN | 109207477 B | 7/2021 |
| CN | 114410609 A | 4/2022 |
| CN | 114438055 A | 5/2022 |
| CN | 114672473 A | 6/2022 |
| CN | 114746125 A | 7/2022 |
| CN | 115572727 A | 1/2023 |
| CN | 115975986 A | 4/2023 |
| CN | 116004573 A | 4/2023 |
| WO | WO-2021226558 A1 * | 11/2021 ........... C12N 15/102 |
| WO | 2023077053 A2 | 5/2023 |

OTHER PUBLICATIONS

Ran, F. A. et al. In vivo genome editing using *Staphylococcus aureus* Cas9. Nature 520, 186-191 (2015). (Year: 2015).*
Zhang, B. et al. Mechanistic insights into the R-loop formation and cleavage in CRISPR-Cas12i1. Nature Communications (2021) 12:3476 (Year: 2021).*
Wei Jiayu, Application of CAS9 D10A and CAS9 H840A in *Escherichia coli* Ge-nome Editing, Genomics and Applied Biology, 2022, pp. 1677-1691, vol. 41, No. 8.
Zhang Yumiao, et al., Research Progress on Improving CRISPR/Cas Genome Editing Efficiency, Chinese Journal of Tropical Crops, 2019, pp. 2006-2015, vol. 40, No. 10.
Yi Yang, et al. Highly Efficient and Rapid Detection of the Cleavage Activity of Cas9/gRNA via a Fluorescent Reporter, Applied Biochemistry and Biotechnology , 2016.

* cited by examiner

*Primary Examiner* — Arthur S Leonard

(74) *Attorney, Agent, or Firm* — Bayramoglu Law Offices LLC

(57) ABSTRACT

An engineered type V Cas protein is provided, including a parental type V Cas protein and an HNH domain. The HNH domain is located at an N-terminus of the parental type V Cas protein; or the HNH domain is located between two continuous or non-continuous amino acids of the parental type V Cas protein, named as a first amino acid and a second amino acid, respectively. The first amino acid and the second amino acid are selected from one of amino acids 1 to 10 at the N-terminus of the parental type V Cas protein, and the first amino acid and the second amino acid are different amino acid positions of the parental type V Cas protein; or the first amino acid and the second amino acid are selected from amino acid positions corresponding to amino acids 794 and 795 of SEQ ID NO: 9.

15 Claims, 4 Drawing Sheets
Specification includes a Sequence Listing.

ENGINEERED CAS PROTEIN AND USE THEREOF

CROSS REFERENCE TO RELATED APPLICATION

This application is a continuation application of International Application No. PCT/CN2023/134558, filed on Nov. 28, 2023, which is based upon and claims priority to a Chinese patent application No. 2023108304381, filed on Jul. 7, 2023, a Chinese patent application No. 2023109616643, filed on Aug. 1, 2023, a Chinese patent application No. 2023110788405, filed on Aug. 25, 2023, and a Chinese patent application No. 2023112304717, filed on Sep. 22, 2023, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBSDSF007-PKG_Sequence_Listing.xml, created on 12/28/2023, and is 67,825 bytes in size.

TECHNICAL FIELD

The present disclosure relates to the field of gene editing, and in particular to the technical field of clustered regularly interspaced short palindromic repeat (CRISPR). Specifically, the present disclosure relates to an engineered Cas protein, and in particular to a type V Cas protein fused with an HNH domain, and use of the type V Cas protein. The present disclosure also provides an HNH domain and use of the HNH domain in improvement of an editing efficiency of a Cas protein.

BACKGROUND

The CRISPR/Cas technology is a widely-used gene editing technology. RNA guidance is used to specifically bind to a target sequence on a genome and cleave DNA to produce double-strand breaks, and site-directed gene editing is conducted through biological non-homologous end joining or homologous recombination.

Type II CRISPR endonucleases, such as Cas9, each include two nuclease domains, an HNH domain, and a RuvC domain. Unlike type II CRISPR endonucleases, type V CRISPR endonucleases, such as Cas12a (also known as cpf1), have merely a RuvC domain and do not include an HNH domain. For example, as documented in a Chinese patent CN109207477B, a Cpf1 protein does not include an HNH nuclease domain contained in a Cas9 protein.

The present disclosure provides an engineered type V Cas enzyme. An HNH domain is fused to the type V Cas enzyme to improve the editing activity of the type V Cas enzyme to a certain extent, which has broad application prospects.

SUMMARY

An HNH domain is fused in a type V Cas enzyme by the inventors to improve an editing activity of the type V Cas enzyme and expand an application range of the type V Cas enzyme.

Engineered Type V Cas Protein

In a first aspect, the present disclosure provides an engineered type V Cas protein including a parental type V Cas protein and an HNH domain, where the HNH domain is located between two continuous or non-continuous amino acids of the parental type V Cas protein.

"The HNH domain is located between two continuous or non-continuous amino acids of the parental type V Cas protein" can mean that the HNH domain is fused between the two continuous or non-continuous amino acids of the parental type V Cas protein or the HNH domain is linked between the two continuous or non-continuous amino acids of the parental type V Cas protein. For example, the two continuous or non-continuous amino acids of the parental type V Cas protein are a first amino acid and a second amino acid, respectively; and one end of the HNH domain is linked to the first amino acid, and the other end of the HNH domain is linked to the second amino acid, where the linking may refer to direct linking or indirect linking through a linker.

The term "linker" is well known in the art when it comes to polypeptide linking, and refers to a chemical group or a molecule that links two molecules or moieties. The linker can be composed of a single linking molecule (such as a single amino acid), or can include more than one linking molecules. In some embodiments, the linker can be an organic molecule, a group, a polymer, or a chemical moiety such as a divalent organic moiety. In some embodiments, the linker can be an amino acid or a peptide.

The linker is well known in the art, and includes, but is not limited to, a linker with one or more (such as 1, 2, 3, 4, or 5) amino acids (such as Glu or Ser) or amino acid derivatives (such as Ahx, β-Ala, GABA, or Ava), or a polyethylene glycol (PEG) linker.

In some embodiments, the linker can be a GS linker. In some embodiments, the linker can include an amino acid sequence: $(GGS)_n$, GS, SG, GSSG (SEQ ID NO: 60), $S(GGS)_n$ (SEQ ID NO: 61), SGGS, or $(GGGGS)_n$ (SEQ ID NO: 62), where n is an integer of 1 to 20 (such as 1, 2, 3, 4, 5, 6, 7, 8, 9, 10, 11, 12, 13, 14, 15, 16, 17, 18, 19, or 20). In some embodiments, the linker may include an amino acid sequence: SGGSGGSGGS (SEQ ID NO: 63). In some embodiments, the linker may include an amino acid sequence: SGSETPGTSESATPES (SEQ ID NO: 64), which is also known as an XTEN linker. In some embodiments, the linker may include an amino acid sequence: SGGSSGGSSGSETPGTSESATPESSGGSSGGS (SEQ ID NO: 65), which is also known as a GS-XTEN-GS linker.

In an embodiment, the two continuous or non-continuous amino acids of the parental type V Cas protein are a first amino acid and a second amino acid, respectively, and the HNH domain is located between the first amino acid and the second amino acid. In an embodiment, the first amino acid and the second amino acid are two continuous amino acids; and in another embodiment, the first amino acid and the second amino acid are two non-continuous amino acids.

In the present disclosure, the HNH domain is a domain with a nuclease cleavage activity, and the HNH domain can be derived from Cas9 or other species. Those skilled in the art can use a conventional technical means to acquire the HNH domain with a nuclease cleavage activity, for example, the HNH domain with a nuclease cleavage activity can be obtained through bioinformatics analysis.

In an embodiment, the HNH domain is selected from one or more of an HNH domain derived from Cas9, an HNH domain derived from *Mycobacterium* phage Severus (Mbps), an HNH domain derived from *Mycobacterium* virus PMC (Mbvp), an HNH domain derived from *Arabidopsis thaliana*, an HNH domain derived from *Papaver somniferum*, an HNH domain derived from *Glycine max*, an HNH domain derived from *Chelonia mydas*, and an HNH domain derived from Halovirus.

In an embodiment, the HNH domain derived from Mbps is derived from an HNH endonuclease of Mbps; and in an embodiment, the HNH endonuclease has an amino acid sequence shown in SEQ ID NO: 12.

In an embodiment, the HNH domain derived from Mbvp is derived from an HNH endonuclease of Mbvp; and in an embodiment, the HNH endonuclease has an amino acid sequence shown in SEQ ID NO: 13.

In an embodiment, the HNH domain derived from *Arabidopsis thaliana* is derived from an HNH endonuclease domain-containing protein of *Arabidopsis thaliana*; and in an embodiment, the HNH endonuclease domain-containing protein has an amino acid sequence shown in SEQ ID NO: 14.

In an embodiment, the HNH domain derived from *Papaver somniferum* is derived from an HNH domain-containing protein of *Papaver somniferum*; and in an embodiment, the HNH domain-containing protein has an amino acid sequence shown in SEQ ID NO: 15.

In an embodiment, the HNH domain derived from *Glycine max* is derived from an HNH endonuclease domain-containing protein of *Glycine max*; and in an embodiment, the HNH endonuclease domain-containing protein has an amino acid sequence shown in SEQ ID NO: 16.

In an embodiment, the HNH domain derived from *Chelonia mydas* is derived from a Zinc finger Ran-binding domain-containing protein of *Chelonia mydas*; and in an embodiment, the Zinc finger Ran-binding domain-containing protein has an amino acid sequence shown in SEQ ID NO: 17.

In an embodiment, the HNH domain derived from Halovirus is derived from an HNH endonuclease of Halovirus; and in an embodiment, the HNH endonuclease has an amino acid sequence shown in SEQ ID NO: 18.

In an embodiment, the HNH domain is an HNH domain derived from Cas9. In an embodiment, an amino acid sequence of the HNH domain derived from Cas9 has at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with SEQ ID NO: 1, and has a biological function of the HNH domain. In an embodiment, an amino acid sequence of the HNH domain derived from Cas9 is obtained through substitution, deletion, or addition of one or more amino acids based on SEQ ID NO: 1, for example, substitution, deletion, or addition of 1 to 20 amino acids, such as substitution, deletion, or addition of 1, 2, 3, 4, 5, 6, 7, 8, 9, 10, 11, 12, 13, 14, 15, 16, 17, 18, 19, or 20 amino acids; and the amino acid sequence of the HNH domain derived from Cas9 has a biological function of the HNH domain. Preferably, an amino acid sequence of the HNH domain derived from Cas9 is shown in SEQ ID NO: 1.

In an embodiment, the HNH domain is an HNH domain derived from Mbps. In an embodiment, an amino acid sequence of the HNH domain derived from Mbps has at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with SEQ ID NO: 2, and has a biological function of the HNH domain. In an embodiment, an amino acid sequence of the HNH domain derived from Mbps is obtained through substitution, deletion, or addition of one or more amino acids based on SEQ ID NO: 2, for example, substitution, deletion, or addition of 1 to 20 amino acids, such as substitution, deletion, or addition of 1, 2, 3, 4, 5, 6, 7, 8, 9, 10, 11, 12, 13, 14, 15, 16, 17, 18, 19, or 20 amino acids; and the amino acid sequence of the HNH domain derived from Mbps has a biological function of the HNH domain. Preferably, an amino acid sequence of the HNH domain derived from Mbps is shown in SEQ ID NO: 2.

In an embodiment, the HNH domain is an HNH domain derived from Mbvp. In an embodiment, an amino acid sequence of the HNH domain derived from Mbvp has at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with SEQ ID NO: 3, and has a biological function of the HNH domain. In an embodiment, an amino acid sequence of the HNH domain derived from Mbvp is obtained through substitution, deletion, or addition of one or more amino acids based on SEQ ID NO: 3, for example, substitution, deletion, or addition of 1 to 20 amino acids, such as substitution, deletion, or addition of 1, 2, 3, 4, 5, 6, 7, 8, 9, 10, 11, 12, 13, 14, 15, 16, 17, 18, 19, or 20 amino acids; and the amino acid sequence of the HNH domain derived from Mbvp has a biological function of the HNH domain. Preferably, an amino acid sequence of the HNH domain derived from Mbvp is shown in SEQ ID NO: 3.

In an embodiment, the HNH domain is an HNH domain derived from *Arabidopsis thaliana*. In an embodiment, an amino acid sequence of the HNH domain derived from *Arabidopsis thaliana* has at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with SEQ ID NO: 4, and has a biological function of the HNH domain. In an embodiment, an amino acid sequence of the HNH domain derived from *Arabidopsis thaliana* is obtained through substitution, deletion, or addition of one or more amino acids based on SEQ ID NO: 4, for example, substitution, deletion, or addition of 1 to 20 amino acids, such as substitution, deletion, or addition of 1, 2, 3, 4, 5, 6, 7, 8, 9, 10, 11, 12, 13, 14, 15, 16, 17, 18, 19, or 20 amino acids; and the amino acid sequence of the HNH domain derived from *Arabidopsis thaliana* has a biological function of the HNH domain. Preferably, an amino acid sequence of the HNH domain derived from *Arabidopsis thaliana* is shown in SEQ ID NO: 4.

In an embodiment, the HNH domain is an HNH domain derived from *Papaver somniferum*.

In an embodiment, an amino acid sequence of the HNH domain derived from *Papaver somniferum* has at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with SEQ ID NO: 5, and has a biological function of the HNH domain. In an embodiment, an amino acid sequence of the HNH domain derived from *Papaver somniferum* is obtained through substitution, deletion, or addition of one or more amino acids based on SEQ ID NO: 5, for example, substitution, deletion, or addition of 1 to 20 amino acids, such as substitution, deletion, or addition of 1, 2, 3, 4, 5, 6, 7, 8, 9, 10, 11, 12, 13, 14, 15, 16, 17, 18, 19, or 20 amino acids; and the amino acid sequence of the HNH domain derived from *Papaver somniferum* has a biological function of the HNH domain. Preferably, an amino acid sequence of the HNH domain derived from *Papaver somniferum* is shown in SEQ ID NO: 5.

In an embodiment, the HNH domain is an HNH domain derived from *Glycine max*. In an embodiment, an amino acid sequence of the HNH domain derived from *Glycine max* has at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with SEQ ID NO: 6, and has a biological function of the HNH domain. In an embodiment, an amino acid sequence of the HNH domain derived from *Glycine max* is obtained through substitution, deletion, or addition of one or more amino acids based on SEQ ID NO: 6, for example, substitution, deletion, or addition of 1 to 20 amino acids, such as substitution, deletion, or addition of 1, 2, 3, 4, 5, 6, 7, 8, 9, 10, 11, 12, 13, 14, 15, 16, 17, 18, 19, or 20 amino acids; and the amino acid sequence of the HNH domain derived from *Glycine max* has a biological function of the HNH domain. Preferably, an amino acid sequence of the HNH domain derived from *Glycine max* is shown in SEQ ID NO: 6.

In an embodiment, the HNH domain is an HNH domain derived from *Chelonia mydas*. In an embodiment, an amino acid sequence of the HNH domain derived from *Chelonia mydas* has at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with SEQ ID NO: 7, and has a biological function of the HNH domain. In an embodiment, an amino acid sequence of the HNH domain derived from *Chelonia mydas* is obtained through substitution, deletion, or addition of one or more amino acids based on SEQ ID NO: 7, for example, substitution, deletion, or addition of 1 to 20 amino acids, such as substitution, deletion, or addition of 1, 2, 3, 4, 5, 6, 7, 8, 9, 10, 11, 12, 13, 14, 15, 16, 17, 18, 19, or 20 amino acids; and the amino acid sequence of the HNH domain derived from *Chelonia mydas* has a biological function of the HNH domain. Preferably, an amino acid sequence of the HNH domain derived from *Chelonia mydas* is shown in SEQ ID NO: 7.

In an embodiment, the HNH domain is an HNH domain derived from Halovirus. In an embodiment, an amino acid sequence of the HNH domain derived from Halovirus has at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with SEQ ID NO: 8, and has a biological function of the HNH domain. In an embodiment, an amino acid sequence of the HNH domain derived from Halovirus is obtained through substitution, deletion, or addition of one or more amino acids based on SEQ ID NO: 8, for example, substitution, deletion, or addition of 1 to 20 amino acids, such as substitution, deletion, or addition of 1, 2, 3, 4, 5, 6, 7, 8, 9, 10, 11, 12, 13, 14, 15, 16, 17, 18, 19, or 20 amino acids; and the amino acid sequence of the HNH domain derived from Halovirus has a biological function of the HNH domain. Preferably, an amino acid sequence of the HNH domain derived from Halovirus is shown in SEQ ID NO: 8.

The biological function of the HNH domain refers to a nuclease cleavage activity exhibited by the HNH domain.

In an embodiment, the parental type V Cas protein is selected from one or more of Cas12i, Cas12j, Cas12a, Cas12b, Cas12d, Cas12e, Cas12f, Cas12g, Cas12h, and Cas-sf0005.

In an embodiment, the parental type V Cas protein is a Cas protein of the Cas12i family, such as Cas12i1, Cas12i2, Cas12i3, or Cas12i12.

In an embodiment, the parental type V Cas protein is a Cas protein of the Cas12j family, such as Cas12j19, and an amino acid sequence of wild-type (WT) Cas12j19 is shown in SEQ ID NO: 19.

The WT Cas12j19 is recorded in a Chinese patent CN111770992B, and is named Cas12j.19 in the Chinese patent CN111770992B. In the present disclosure, the WT Cas12j19 is called Cas12j19.

Mutated Cas12j19 obtained through site-directed mutagenesis of an amino acid in Cas12j19 can also be used as the parental type V Cas protein of the present disclosure, such as Cas12j19 mutants obtained through amino acid mutations recorded in Chinese patent applications 2023100922319 and 2023110952452.

In an embodiment, the mutated Cas12j19 is obtained through a mutation of any one or more of amino acids 100, 400, 763, and 45 in the amino acid sequence shown in SEQ ID NO: 19.

In an embodiment, the mutated Cas12j19 is obtained through a mutation of an amino acid 100 in the amino acid sequence shown in SEQ ID NO: 19.

In an embodiment, the mutated Cas12j19 is obtained through a mutation of amino acids 100, 400, and 763 in the amino acid sequence shown in SEQ ID NO: 19.

In an embodiment, the mutated Cas12j19 is obtained through a mutation of amino acids 100, 400, 763, and 45 in the amino acid sequence shown in SEQ ID NO: 19.

In an embodiment, the amino acid 100 is mutated into an amino acid rather than E, such as A, V, G, L, S, F, W, Y, N, D, Q, K, M, T, C, P, H, R, or I, and is preferably mutated into K.

In an embodiment, the amino acid 400 is mutated into an amino acid rather than S, such as A, V, G, Y, D, F, W, L, N, E, Q, K, M, T, C, P, H, R, or I, and is preferably mutated into R.

In an embodiment, the amino acid 763 is mutated into an amino acid rather than L, such as A, V, G, Y, D, F, W, S, N, E, Q, K, M, T, C, P, H, R, or I, and is preferably mutated into R.

In an embodiment, the amino acid 45 is mutated into an amino acid rather than S, such as A, V, G, Y, D, F, W, L, N, E, Q, K, M, T, C, P, H, R, or I, and is preferably mutated into T.

In an embodiment, the parental type V Cas protein is the WT Cas12j19 or the mutated Cas12j19.

In an embodiment, the parental type V Cas protein is Cas12a, such as FnCas12a, AsCas12a, LbCas12a, Lb5Cas12a, HkCas12a, OsCas12a, TsCas12a, BbCas12a, BoCas12a, or Lb4Cas12a, and is preferably LbCas12a.

In an embodiment, the parental type V Cas protein is Cas-sf0005.

In some embodiments, the parental type V Cas protein is a natural WT Cas protein; and in some other embodiments, the parental type V Cas protein is an engineered Cas protein, such as a Cas protein obtained through site-directed mutagenesis of an amino acid.

In a preferred embodiment, the parental type V Cas protein is WT Cas12i3, and an amino acid sequence of the WT Cas12i3 (which is called Cas12f.4 in CN111757889B and is called Cas12i3 in the present disclosure) is shown in SEQ ID NO: 9.

In a preferred embodiment, the parental type V Cas protein is Cas12a such as LbCas12a, and an amino acid sequence of the Cas12a is shown in SEQ ID NO: 10.

In a preferred embodiment, the parental type V Cas protein is Cas-sf0005, and an amino acid sequence of the Cas-sf0005 is shown in SEQ ID NO: 11.

In an embodiment, the amino acid sequence of the parental type V Cas protein has at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with SEQ ID NO: 9, SEQ ID NO: 19, SEQ ID NO: 10, or SEQ ID NO: 11.

In an embodiment, the amino acid sequence of the parental type V Cas protein is obtained through substitution, deletion, or addition of one or more amino acids based on SEQ ID NO: 9, SEQ ID NO: 19, SEQ ID NO: 10, or SEQ ID NO: 11, for example, substitution, deletion, or addition of 1 to 20 amino acids, such as substitution, deletion, or addition of 1, 2, 3, 4, 5, 6, 7, 8, 9, 10, 11, 12, 13, 14, 15, 16, 17, 18, 19, or 20 amino acids.

A mutated Cas protein obtained through site-directed mutagenesis of an amino acid in Cas12i3, Cas12a, or Cas-sf0005 can also be used as the parental type V Cas protein of the present disclosure.

In an embodiment, mutated Cas12i3 obtained through site-directed mutagenesis of an amino acid in Cas12i3 can be used as the parental type V Cas protein of the present disclosure, such as Cas12i3 mutants obtained through amino acid mutations recorded in Chinese patent applications 2022103148077, 2022102697541, 2022106036073, 2022109432359, 2023100884374, 2023100667809, and 2023104503761.

In an embodiment, the mutated Cas12i3 is obtained through a mutation of any one or more of amino acids 7, 233, 267, 369, 433, 165, 166, 854, 266, 235, 328, and 599 of the amino acid sequence shown in SEQ ID NO: 9; and preferably, the amino acid 7, 233, 267, 369, 433, 165, 166, 854, 266, 235, 328, or 599 is mutated into R.

In an embodiment, the mutated Cas12i3 is obtained through a mutation of an amino acid 7 in the amino acid sequence shown in SEQ ID NO: 9.

In an embodiment, the mutated Cas12i3 is obtained through a mutation of amino acids 7, 233, 267, 369, and 433 in the amino acid sequence shown in SEQ ID NO: 9.

In an embodiment, the mutated Cas12i3 is obtained through a mutation of amino acids 165, 166, 267, and 854 in the amino acid sequence shown in SEQ ID NO: 9.

In an embodiment, the mutated Cas12i3 is obtained through a mutation of amino acids 266, 235, 328, and 599 in the amino acid sequence shown in SEQ ID NO: 9.

In a preferred embodiment, the above amino acid 7, 233, 267, 369, 433, 165, 166, 854, 266, 235, 328, or 599 of the amino acid sequence shown in SEQ ID NO: 9 is mutated into R.

In an embodiment, the mutated Cas12i3 is obtained through a mutation of any one or more of amino acids 619 and 844 of the amino acid sequence shown in SEQ ID NO: 9; and preferably, the amino acid 619 or 844 is mutated into A.

In an embodiment, the parental type V Cas protein is the WT Cas12i3 or the mutated Cas12i3.

In an embodiment, the amino acid sequence of the parental type V Cas protein is obtained through substitution, deletion, or addition of one or more amino acids based on SEQ ID NO: 11. In an embodiment, the parental type V Cas protein is obtained through a mutation of any one or more of amino acids 6, 149, 351, and 667 in the amino acid sequence shown in SEQ ID NO: 11; and preferably, the amino acids 6, 149, 351, and 667 all are mutated into R.

In an embodiment, the two continuous or non-continuous amino acids of the parental type V Cas protein are a first amino acid and a second amino acid, respectively, and the HNH domain is located between the first amino acid and the second amino acid.

In an embodiment, the HNH domain is located at an N-terminus of the parental type V Cas protein.

In the present disclosure, "the HNH domain is located at an N-terminus of the parental type V Cas protein" can means that the HNH domain is located between an amino acid 1 (usually methionine) and an amino acid 2 from the N-terminus of the parental type V Cas protein. In some embodiments, the parental type V Cas protein may not include a starting amino acid (such as methionine) of the N-terminus, in which case the HNH domain can be directly linked to the N-terminus of the parental type V Cas protein, that is, the HNH domain is fused to the N-terminus of the parental type V Cas protein.

In an embodiment, the first amino acid and the second amino acid are an amino acid 1 and an amino acid 2 from the N-terminus of the parental type V Cas protein, and the amino acid 1 from the N-terminus of the parental type V Cas protein is usually a starting amino acid (generally methionine).

In the present disclosure, the HNH domain is located between an amino acid 1 and an amino acid 2 of an N-terminus of a type V Cas protein (such as Cas12i3, Cas12j19, Cas12a, or Cas-sf0005) to improve an editing activity of the type V Cas protein.

In an embodiment, the HNH domain is located between two continuous or non-continuous amino acids of the parental type V Cas protein, where the two continuous or non-continuous amino acids of the parental type V Cas protein are a first amino acid and a second amino acid, respectively, the HNH domain is located between the first amino acid and the second amino acid, the first amino acid and the second amino acid are selected from any one of amino acids 1 to 10 (an amino acid 1, 2, 3, 4, 5, 6, 7, 8, 9, or 10) at the N-terminus of the parental type V Cas protein, and the first amino acid and the second amino acid are different amino acid positions of the parental type V Cas protein.

In an embodiment, the first amino acid is selected from any one of amino acid positions corresponding to amino acids 1 to 10 (an amino acid 1, 2, 3, 4, 5, 6, 7, 8, 9, or 10) of SEQ ID NO: 9, the second amino acid is selected from any one of amino acid positions corresponding to amino acids 1 to 10 (an amino acid 1, 2, 3, 4, 5, 6, 7, 8, 9, or 10) of SEQ ID NO: 9, and the first amino acid and the second amino acid are different amino acid positions corresponding to SEQ ID NO: 9.

In an embodiment, the first amino acid is selected from any one of amino acid positions corresponding to amino acids 1 to 10 (an amino acid 1, 2, 3, 4, 5, 6, 7, 8, 9, or 10) of SEQ ID NO: 19, the second amino acid is selected from any one of amino acid positions corresponding to amino acids 1 to 10 (an amino acid 1, 2, 3, 4, 5, 6, 7, 8, 9, or 10) of SEQ ID NO: 19, and the first amino acid and the second amino acid are different amino acid positions corresponding to SEQ ID NO: 19.

In an embodiment, the first amino acid and the second amino acid are selected from any one of the following amino acid sets corresponding to SEQ ID NO: 9:
  an amino acid 1 and an amino acid 2;
  an amino acid 2 and an amino acid 3;
  an amino acid 3 and an amino acid 4;
  an amino acid 4 and an amino acid 5;
  an amino acid 5 and an amino acid 6;
  an amino acid 6 and an amino acid 7;
  an amino acid 7 and an amino acid 8;
  an amino acid 8 and an amino acid 9; and
  an amino acid 9 and an amino acid 10.

In an embodiment, the first amino acid and the second amino acid are any one of the following amino acid sets corresponding to SEQ ID NO: 9: an amino acid 1 and an amino acid 2, an amino acid 2 and an amino acid 3, an amino acid 3 and an amino acid 4, an amino acid 4 and an amino acid 5, an amino acid 5 and an amino acid 6, an amino acid 6 and an amino acid 7, an amino acid 7 and an amino acid 8, an amino acid 8 and an amino acid 9, and an amino acid 9 and an amino acid 10. In this embodiment, the HNH domain is located between the first amino acid and the second amino acid of the parental type V Cas protein, the first amino acid and the second amino acid of the parental type V Cas protein are the amino acid positions corresponding to the amino acid 1 and the amino acid 2, the amino acid 2 and the amino acid 3, the amino acid 3 and the amino acid 4, the amino acid 4 and the amino acid 5, the amino acid 5 and the amino acid 6, the amino acid 6 and the amino acid 7, the amino acid 7 and the amino acid 8, the amino acid 8 and the amino acid 9, or the amino acid 9 and the amino acid 10 of SEQ ID NO: 9.

In an embodiment, the first amino acid and the second amino acid are selected from any one of the following amino acid sets corresponding to SEQ ID NO: 19:
  an amino acid 1 and an amino acid 2;
  an amino acid 2 and an amino acid 3;
  an amino acid 3 and an amino acid 4;
  an amino acid 4 and an amino acid 5;
  an amino acid 5 and an amino acid 6;
  an amino acid 6 and an amino acid 7;
  an amino acid 7 and an amino acid 8;
  an amino acid 8 and an amino acid 9; and
  an amino acid 9 and an amino acid 10.

In an embodiment, the first amino acid and the second amino acid are any one of the following amino acid sets corresponding to SEQ ID NO: 19: an amino acid 1 and an amino acid 2, an amino acid 2 and an amino acid 3, an amino acid 3 and an amino acid 4, an amino acid 4 and an amino acid 5, an amino acid 5 and an amino acid 6, an amino acid 6 and an amino acid 7, an amino acid 7 and an amino acid 8, an amino acid 8 and an amino acid 9, and an amino acid 9 and an amino acid 10. In this embodiment, the HNH domain is located between the first amino acid and the second amino acid of the parental type V Cas protein, the first amino acid and the second amino acid of the parental type V Cas protein are the amino acid positions corresponding to the amino acid 1 and the amino acid 2, the amino acid 2 and the amino acid 3, the amino acid 3 and the amino acid 4, the amino acid 4 and the amino acid 5, the amino acid 5 and the amino acid 6, the amino acid 6 and the amino acid 7, the amino acid 7 and the amino acid 8, the amino acid 8 and the amino acid 9, or the amino acid 9 and the amino acid 10 of SEQ ID NO: 19.

In an embodiment, the first amino acid and the second amino acid are selected from amino acid positions corresponding to amino acids 1 and 2 of SEQ ID NO: 10.

In an embodiment, the first amino acid and the second amino acid are selected from amino acid positions corresponding to amino acids 1 and 2 of SEQ ID NO: 11.

In an embodiment, the first amino acid and the second amino acid are amino acid positions corresponding to amino acids 794 and 795 of SEQ ID NO: 9. In this embodiment, the HNH domain is located between the first amino acid and the second amino acid of the parental type V Cas protein, the first amino acid and the second amino acid of the parental type V Cas protein are the amino acid positions corresponding to the amino acids 794 and 795 of SEQ ID NO: 9.

The amino acid position in the present disclosure refers to a position from an N-terminus of an amino acid sequence, for example, an amino acid 2 of an amino acid sequence shown in SEQ ID NO: 9 refers to the second amino acid of SEQ ID NO: 9 from its N-terminus.

In an embodiment, the engineered type V Cas protein of the present disclosure is selected from any one of the following I to III:
  I. The engineered type V Cas protein includes a parental type V Cas protein and an HNH domain, where the HNH domain is located between two continuous or non-continuous first and second amino acids of the parental type V Cas protein;
  An amino acid sequence of the parental type V Cas protein is shown in SEQ ID NO: 9, SEQ ID NO: 19, SEQ ID NO: 10, or SEQ ID NO: 11; or
  the amino acid sequence of the parental type V Cas protein has at least 80% sequence identity with SEQ ID NO: 9, SEQ ID NO: 19, SEQ ID NO: 10, or SEQ ID NO: 11; or
  the amino acid sequence of the parental type V Cas protein is obtained through substitution, deletion, or addition of one or more amino acids (such as substitution, deletion, or addition of 1, 2, 3, 4, 5, 6, 7, 8, 9, 10, 11, 12, 13, 14, 15, 16, 17, 18, 19, or 20 amino acids) based on SEQ ID NO: 9, SEQ ID NO: 19, SEQ ID NO: 10, or SEQ ID NO: 11; or
  the parental type V Cas protein is obtained through a mutation of any one or more of amino acids 7, 233, 267, 369, 433, 165, 166, 854, 266, 235, 328, and 599 in an amino acid sequence shown in SEQ ID NO: 9; or
  the parental type V Cas protein is obtained through a mutation of any one or more of amino acids 100, 400, 763, and 45 in an amino acid sequence shown in SEQ ID NO: 19; or
  the parental type V Cas protein is obtained through a mutation of any one or more of amino acids 6, 149, 351, and 667 in an amino acid sequence shown in SEQ ID NO: 11;
  The HNH domain is selected from one or more of an HNH domain derived from Cas9, an HNH domain derived from Mbps, an HNH domain derived from Mbvp, an HNH domain derived from *Arabidopsis thaliana*, an HNH domain derived from *Papaver somniferum*, an HNH domain derived from *Glycine max*, an HNH domain derived from *Chelonia mydas*, and an HNH domain derived from Halovirus;
  The first amino acid and the second amino acid are selected from any one of amino acids 1 to 10 (an amino acid 1, 2, 3, 4, 5, 6, 7, 8, 9, or 10) at an N-terminus of the parental type V Cas protein, and the first amino acid and the second amino acid are different amino acid positions of the parental type V Cas protein; or the first amino acid is selected from any one of amino acid positions corresponding to amino acids 1 to 10 (an amino acid 1, 2, 3, 4, 5, 6, 7, 8, 9, or 10) of SEQ ID NO: 9, the second amino acid is selected from any one of amino acid positions corresponding to amino acids 1 to 10 (an amino acid 1, 2, 3, 4, 5, 6, 7, 8, 9, or 10) of SEQ ID NO: 9, and the first amino acid and the second amino acid are different amino acid positions corresponding to SEQ ID NO: 9; or the first amino acid is selected from any one of amino acid positions corresponding to amino acids 1 to 10 (an amino acid 1, 2, 3, 4, 5, 6, 7, 8, 9, or 10) of SEQ ID NO: 19, the second amino acid is selected from any one of amino acid positions corresponding to amino acids 1 to 10 (an amino acid 1, 2, 3, 4, 5, 6, 7, 8, 9, or 10) of SEQ ID NO: 19, and the first amino acid and the second amino acid are different amino acid positions corresponding to SEQ ID NO: 19;

II. The engineered type V Cas protein has at least 80%, at least 85%, at least 90%, at least 91%, at least 92%, at least 93%, at least 94%, at least 95%, at least 96%, at least 97%, at least 98%, or at least 99% sequence identity with the engineered type V Cas protein described in I, and basically retains biological functions of the engineered type V Cas protein described in I;

III. The engineered type V Cas protein is obtained through substitution, deletion, or addition of one or more amino acids based on the engineered type V Cas protein described in I, for example, substitution, deletion, or addition of 1 to 20 amino acids, such as substitution, deletion, or addition of 1, 2, 3, 4, 5, 6, 7, 8, 9, 10, 11, 12, 13, 14, 15, 16, 17, 18, 19, or 20 amino acids; and the engineered type V Cas protein basically retains biological functions of the engineered type V Cas protein described in I.

The biological functions of the engineered type V Cas protein include: a biological function of the parental type V Cas protein, such as an activity to bind to guide RNA (gRNA), an endonuclease activity, or an activity to bind to a specific position of a target sequence and cleave the target sequence under guidance of gRNA (including but not limited to Cis cleavage activity and Trans cleavage active); and an additional nuclease cleavage activity produced after fusion of an HNH domain.

It is clear to those skilled in the art that a structure of a protein can be changed without adversely affecting the activity and functionality of the protein. For example, one or more conservative amino acid substitutions can be introduced into an amino acid sequence of a protein without adversely affecting an activity and/or three-dimensional (3D) structure of a protein molecule. Those skilled in the art are aware of examples and implementations of the conservative amino acid substitutions. Specifically, an amino acid residue can be substituted by another amino acid residue that belongs to the same group as the amino acid residue to be substituted. That is, a nonpolar amino acid residue can be substituted by another nonpolar amino acid residue; an uncharged polar amino acid residue can be substituted by another uncharged polar amino acid residue; a basic amino acid residue can be substituted by another basic amino acid residue; and an acidic amino acid residue can be substituted by another acidic amino acid residue. Such substituted amino acid residues may be or may not be encoded by genetic codes. As long as a substitution does not result in a loss of a biological activity of a protein, a conservative substitution in which an amino acid is substituted by another amino acid belonging to the same group falls within the scope of the present disclosure. Therefore, the engineered type V Cas protein of the present disclosure may include one or more conservative substitutions in its amino acid sequence, and these conservative substitutions may be preferably generated according to Table 1. In addition, the present disclosure also covers proteins with one or more other non-conservative substitutions, as long as the non-conservative substitutions do not significantly affect the desired function and biological activity of the protein of the present disclosure.

Conservative amino acid substitutions can be made at one or more predicted non-essential amino acid residues. Non-essential amino acid residues are amino acid residues that can be changed (deleted or substituted) without changing a biological activity, while essential amino acid residues are required for a biological activity. A conservative amino acid substitution refers to a substitution in which an amino acid residue is substituted by an amino acid residue with a similar side chain. An amino acid substitution can be made in a non-conservative region of the engineered type V Cas protein. Generally, such a substitution is not made to a conservative amino acid residue or an amino acid residue located within a conservative motif, because such a residue is required for an activity of a protein. However, those skilled in the art should understand that a functional variant may have few conservative or non-conservative variations in a conservative region.

TABLE 1

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

It is well known in the art that one or more amino acid residues can be changed (substituted, deleted, truncated, or inserted) at an N-terminus and/or C-terminus of a protein while still retaining a functional activity of the protein. Therefore, a protein obtained by changing one or more amino acid residues at an N-terminus and/or C-terminus of a Cas protein while retaining a desired functional activity of the Cas protein is also within the scope of the present disclosure. The change may include a change introduced by a modern molecular method such as polymerase chain reaction (PCR), and the modern molecular method includes PCR amplification that alters or extends a protein coding sequence by introducing an amino acid coding sequence into an oligonucleotide used for the PCR amplification.

It should be recognized that a protein can be altered in various ways, including amino acid substitution, deletion, truncation, and insertion, and methods for such operations are generally known in the art. For example, amino acid sequence variants of the protein can be prepared through a mutation of DNA. It can also be completed through other mutagenesis forms and/or through directed evolution, for example, known mutagenesis, recombination, and/or shuffling methods can be used in combination with a related screening method to allow substitution, deletion, and/or insertion of one or more amino acids.

Those skilled in the art can understand that these small amino acid changes in the Cas protein of the present disclosure can be naturally present (for example, natural mutations) or can be induced (for example, using r-DNA technology) without affecting a function or activity of the Cas protein. If these mutations occur in a catalytic domain, an active site, or another functional domain of a protein, properties of the protein may be changed, but the protein may retain its activity. If existing mutations are not close to a catalytic domain, an active site, or another functional domain, it can be expected that there is a small impact.

Those skilled in the art can identify essential amino acids of the engineered type V Cas protein of the present disclosure according to a method known in the art, such as site-directed mutagenesis or protein evolution or bioinformatics analysis. The catalytic domain, active site, or another functional domain of the protein can also be determined through physical analysis of a structure of the protein, for example, it can be determined through a technique such as nuclear magnetic resonance (NMR), crystallography, electron diffraction, or photoaffinity labeling in combination with a putative amino acid mutation at a key site.

In the present disclosure, an amino acid residue can be represented by a single letter or three letters, such as: alanine (Ala, A), valine (Val, V), glycine (Gly, G), leucine (Leu, L), glutamine (Gln, Q), phenylalanine (Phe, F), tryptophan (Trp, W), tyrosine (Tyr, Y), aspartic acid (Asp, D), asparagine (Asn, N), glutamic acid (Glu, E), lysine (Lys, K), methionine (Met, M), serine (Ser, S), threonine (Thr, T), cysteine (Cys, C), proline (Pro, P), isoleucine (Ile, I), histidine (His, H), and arginine (Arg, R).

The term "AxxB" means that an amino acid A at xx is changed into an amino acid B, for example, E5R means that E at 5 is mutated into R. When there are mutations at a plurality of amino acid positions, the mutations can be expressed in a form such as E5R-V4R, for example, E5R-V4R means that E at 5 is mutated into R while V at 4 is mutated into R.

A specific amino acid position (number) in the protein of the present disclosure is determined by aligning an amino acid sequence of the target protein with a reference amino acid sequence (such as SEQ ID NO: 9 or SEQ ID NO: 19) using a standard sequence alignment tool. For example, the Smith-Waterman algorithm or the CLUSTALW2 algorithm is used to align two sequences, and it is considered that the sequences are aligned when an alignment score is the highest. The alignment score can be calculated according to the method described in Wilbur, W. J. and Lipman, D. J. (1983) Rapid similarity searches of nucleic acid and protein data banks. Proc. Natl. Acad. Sci. USA, 80: 726-730. In the ClustalW2(1.82) algorithm, default parameters may be preferably used: protein gap opening penalty=10.0; protein gap extension penalty=0.2; protein matrix=Gonnet; protein/DNA end gap=−1; and protein/DNAGAPDIST=4. The AlignX program (a part of the vectorNTI group) may preferably be used to align an amino acid sequence of a protein with SEQ ID NO: 9 or SEQ ID NO: 19 using default parameters suitable for multiple alignments (gap opening penalty: 10.0; and gap extension penalty: 0.05) to determine a position of a specific amino acid within the protein.

The present disclosure also provides a fusion protein including the engineered type V Cas protein described above and a modification part.

In an embodiment, the modification part is selected from another protein or polypeptide, a detectable marker, or any combination thereof.

In an embodiment, the modification part is selected from an epitope tag, a reporter gene sequence, a nuclear localization signal (NLS) sequence, a targeting moiety, a transcriptional activation domain (such as VP64), a transcriptional repression domain (such as a KRAB or SID domain), a nuclease domain (such as Fok1), and a domain with an activity selected from a nucleotide deaminase activity (such as an adenosine deaminase or cytidine deaminase activity), a methylase activity, a demethylase activity, a transcription activation activity, a transcription repression activity, a transcription release factor activity, a histone modification activity, a nuclease activity, a single-stranded RNA cleavage activity, a double-stranded RNA cleavage activity, a single-stranded DNA cleavage activity, a double-stranded DNA cleavage activity, and a nucleic acid binding activity; and any combination thereof. The NLS sequence is well known to those skilled in the art, and examples thereof include, but are not limited to, SV40 large T antigen, EGL-13, c-Myc, and TUS protein.

In an embodiment, the NLS sequence is located at, close to, or proximate to a terminus (such as an N-terminus, a C-terminus, or both termini) of the Cas protein of the present disclosure.

The epitope tag is well known to those skilled in the art, including but not limited to His, V5, FLAG, HA, Myc, VSV-G, and Trx; and those skilled in the art can select other suitable epitope tags (such as a purification, detection, or tracing tag).

The reporter gene sequence is well known to those skilled in the art, and examples thereof include but are not limited to GST, HRP, CAT, GFP, HcRed, DsRed, CFP, YFP, and BFP.

In an embodiment, the fusion protein of the present disclosure includes a domain capable of binding to a DNA molecule or an intracellular molecule, such as a maltose-binding protein (MBP), a DNA binding domain (DBD) of Lex A, and DBD of GAL4.

In an embodiment, the fusion protein of the present disclosure includes a detectable marker, such as a fluorescent dye, such as fluorescein isothiocyanate (FITC) or 4',6-diamidino-2-phenylindole (DAPI).

In an embodiment, the engineered type V Cas protein of the present disclosure is optionally coupled to, conjugated with, or fused to the modification part through a linker.

In an embodiment, the modification part is directly linked to an N-terminus or a C-terminus of the engineered type V Cas protein of the present disclosure.

In an embodiment, the modification part may be linked to an N-terminus or a C-terminus of the engineered type V Cas protein of the present disclosure through a linker. The linker is well known in the art, and examples thereof include, but are not limited to, a linker with one or more (such as 1, 2, 3, 4, or 5) amino acids (such as Glu or Ser) or amino acid derivatives (such as Ahx, (3-Ala, GABA, or Ava), or a PEG linker.

A production method of the engineered type V Cas protein, protein derivative, or fusion protein of the present disclosure is not limited. For example, the engineered type V Cas protein, protein derivative, or fusion protein can be produced by a genetic engineering method (recombinant technology), or can be produced by a chemical synthesis method.

Nucleic Acids of the Engineered Type V Cas Protein

In a second aspect, the present disclosure provides an isolated polynucleotide, including:
- (a) a polynucleotide sequence encoding the engineered type V Cas protein or the fusion protein of the present disclosure; or
- a polynucleotide complementary to the polynucleotide described in (a).

In an embodiment, the polynucleotide sequence is codon-optimized for expression in a prokaryotic cell. In an embodiment, the polynucleotide sequence is codon-optimized for expression in a eukaryotic cell.

In an embodiment, the cell is an animal cell, such as a mammalian cell.

In an embodiment, the cell is a human cell.

In an embodiment, the cell is a plant cell, such as a cell possessed by a cultivated plant (such as *Manihot esculenta, Zea mays, Sorghum bicolor, Triticum aestivum*, or *Oryza sativa*), an alga, a tree, or a vegetable.

In an embodiment, the polynucleotide is preferably single-stranded or double-stranded.

gRNA

In a third aspect, the present disclosure provides a gRNA, including a first segment and a second segment. The first segment is also called a "framework region", "protein binding segment", "protein binding sequence", or "direct repeat"; and the second segment is also called a "nucleic acid-targeted targeting sequence", "nucleic acid-targeted targeting segment", or "target sequence-targeted guide sequence".

The first segment of the gRNA can interact with the Cas protein of the present disclosure, such that the Cas protein and the gRNA produce a complex.

In a preferred embodiment, the first segment is the direct repeat.

The nucleic acid-targeted targeting sequence or the nucleic acid-targeted targeting segment of the present disclosure includes a nucleotide sequence complementary to a sequence in a target nucleic acid. In other words, the nucleic acid-targeted targeting sequence or the nucleic acid-targeted targeting segment of the present disclosure can interact with a target nucleic acid in a sequence-specific manner through hybridization (namely, base pairing). Therefore, the nucleic acid-targeted targeting sequence or the nucleic acid-targeted targeting segment can be changed, or can be modified to hybridize with any desired sequence in a target nucleic acid. The nucleic acid is selected from DNA or RNA.

The nucleic acid-targeted targeting sequence or the nucleic acid-targeted targeting segment has at least 60% (such as at least 65%, at least 70%, at least 75%, at least 80%, at least 85%, at least 90%, at least 95%, at least 97%, at least 98%, at least 99%, or 100%) complementarity with a target sequence of a target nucleic acid.

The "framework region", "protein binding segment", "protein binding sequence", or "direct repeat" of the gRNA of the present disclosure can interact with the CRISPR protein (or Cas protein).

The gRNA of the present disclosure guides the Cas protein interacting therewith to a specific nucleotide sequence in a target nucleic acid under an action of the nucleic acid-targeted targeting sequence.

Preferably, the gRNA includes a first segment and a second segment in a direction from 5'-terminus to 3-terminus.

In the present disclosure, the second segment can also be understood as a guide sequence to hybridize with a target sequence.

The gRNA of the present disclosure can produce a complex with the Cas protein.

Vector

The present disclosure also provides a vector, including the engineered type V Cas protein, the isolated nucleic acid, or the polynucleotide described above. Preferably, the vector may further include a regulatory element operably linked to the engineered type V Cas protein, the isolated nucleic acid, or the polynucleotide.

In an embodiment, the regulatory element is one or more selected from the group consisting of an enhancer, a transposon, a promoter, a terminator, a leader sequence, a polyadenylate sequence, and a marker gene.

In an embodiment, the vector may include a cloning vector, an expression vector, a shuttle vector, and an integration vector.

In some embodiments, a vector included in the system is a viral vector (such as a retroviral vector, a lentiviral vector, an adenoviral vector, an adeno-associated virus vector, or a herpes simplex virus vector), or may be a plasmid, a virus, a cosmid, or a phage, which are well known to those skilled in the art.

CRISPR System

The present disclosure provides an engineered non-natural vector system or a CRISPR-Cas system, including: the engineered type V Cas protein or a nucleic acid sequence encoding the engineered type V Cas protein, and a nucleic acid encoding one or more gRNAs.

In an embodiment, the nucleic acid sequence encoding the engineered type V Cas protein and the nucleic acid encoding one or more gRNAs are artificially synthesized.

In an embodiment, the nucleic acid sequence encoding the engineered type V Cas protein and the nucleic acid encoding one or more gRNAs do not co-exist naturally.

The one or more gRNAs target one or more target sequences in a cell. The one or more target sequences hybridize with a genomic locus of a DNA molecule encoding one or more gene products, and guide the Cas protein to the genomic locus of the DNA molecule encoding the one or more gene products; and after the Cas protein reaches a position of the target sequence, the target sequence is modified, edited, or cleaved, such that the expression of the one or more gene products is changed or modified.

The cell of the present disclosure includes one or more of an animal cell, a plant cell, or a microorganism.

In some embodiments, the Cas protein is codon-optimized for expression in a cell.

In some embodiments, the Cas protein guides the cleavage of one or two strands at the position of the target sequence.

The present disclosure also provides an engineered non-natural vector system, including one or more vectors, where the one or more vectors each include:
- a) a first regulatory element operably linked to gRNA and
- b) a second regulatory element operably linked to the Cas protein,
  where the components (a) and (b) are located on the same vector or different vectors of the system.

The first and second regulatory elements each include a promoter (such as a constitutive promoter or an inducible promoter), an enhancer (such as a 35S promoter or a 35S enhanced promoter), an internal ribosome entry site (IRES), and other expression control elements (such as a transcriptional termination signal, such as a polyadenylation signal and a poly-U sequence).

In some embodiments, a vector in the system is a viral vector (such as a retroviral vector, a lentiviral vector, an adenoviral vector, an adeno-associated virus vector, and a herpes simplex virus vector), or may be a plasmid, a virus, a cosmid, or a phage, which are well known to those skilled in the art.

In some embodiments, the system provided herein is in a delivery system. In some embodiments, the delivery system is a nanoparticle, a liposome, an exosome, a microvesicle, or a gene gun.

In an embodiment, the target sequence is a DNA or RNA sequence derived from a prokaryotic cell or a eukaryotic cell. In an embodiment, the target sequence is a non-natural DNA or RNA sequence.

In an embodiment, the target sequence is present in a cell. In an embodiment, the target sequence is present in a nucleus or cytoplasm (such as an organelle). In an embodiment, the cell is a eukaryotic cell. In other embodiments, the cell is a prokaryotic cell.

In an embodiment, the Cas protein is linked to one or more NLS sequences. In an embodiment, the fusion protein includes one or more NLS sequences. In an embodiment, the NLS sequence is linked to an N-terminus or a C-terminus of the protein. In an embodiment, the NLS sequence is fused to an N-terminus or a C-terminus of the protein.

In a fourth aspect, the present disclosure relates to an engineered CRISPR system, including the Cas protein and one or more gRNAs, where the one or more gRNAs include a direct repeat and a spacer capable of hybridizing with a target nucleic acid, and the Cas protein can bind to the gRNA and target the target nucleic acid complementary to the spacer.

Protein-Nucleic Acid Complex/Composition

In a fifth aspect, the present disclosure provides a complex or a composition, including:
 (i) a protein component selected from the engineered type V Cas protein, a derivatized protein, a fusion protein, and any combination thereof, and
 (ii) a nucleic acid component including: (a) a guide sequence capable of hybridizing with a target sequence and (b) a direct repeat capable of binding to the engineered type V Cas protein of the present disclosure,
 where the protein component and the nucleic acid component combine with each other to produce a complex.

In an embodiment, the nucleic acid component is a gRNA in the CRISPR-Cas system.

In an embodiment, the complex or the composition is non-natural or modified. In an embodiment, at least one component in the complex or the composition is non-natural or modified.

In an embodiment, the first component is non-natural or modified; and/or, the second component is non-natural or modified.

Activated CRISPR Complex

In a sixth aspect, the present disclosure also provides an activated CRISPR complex, including: (1) a protein component selected from the engineered type V Cas protein of the present disclosure, a derivatized protein, a fusion protein, and any combination thereof, (2) a gRNA including: (a) a guide sequence capable of hybridizing with a target sequence and (b) a direct repeat capable of binding to the Cas protein of the present disclosure; and (3) a target sequence binding to the gRNA. Preferably, the binding refers to binding between a nucleic acid-targeted targeting sequence on the gRNA and a target nucleic acid.

The term "activated CRISPR complex", "activated complex", or "ternary complex" as used herein refers to a complex obtained after the Cas protein and gRNA in the CRISPR system bind to or are modified by a target nucleic acid.

The Cas protein and gRNA of the present disclosure can produce a binary complex that is activated when binding to a nucleic acid substrate to produce an activated CRISPR complex, where the nucleic acid substrate is complementary to a spacer (or called a guide sequence to hybridize with the target nucleic acid) in the gRNA. In some embodiments, a spacer of the gRNA exactly matches a target substrate. In other embodiments, the spacer of the gRNA matches a portion (continuous or non-continuous) of the target substrate.

In a preferred embodiment, the activated CRISPR complex may exhibit collateral nuclease cleavage activity, and the collateral nuclease cleavage activity refers to non-specific cleavage activity or disordered cleavage activity (which is also called trans cleavage activity in the art) of the activated CRISPR complex on a single-stranded nucleic acid.

Delivery and Delivery Composition

The engineered type V Cas protein, gRNA, fusion protein, nucleic acid, vector, system, complex, and composition of the present disclosure can be delivered by any method known in the art. Such a method includes, but is not limited to, electroporation, lipofection, nucleofection, microinjection, sonoporation, gene gun, calcium phosphate-mediated transfection, cationic lipid transfection, lipofectin transfection, dendritic transfection, heat-shock transfection, nucleofection, magnetofection, lipofection, puncture transfection, optical transfection, reagent-enhanced nucleic acid intake, and delivery through a liposome, an immunoliposome, a viral particle, an artificial virus, or the like.

Therefore, in a seventh aspect, the present disclosure provides a delivery composition, which includes a delivery vehicle and one or more selected from the engineered type V Cas protein, the fusion protein, the nucleic acid, the vector, the system, the complex, and the composition of the present disclosure.

In an embodiment, the delivery vehicle is a particle.

In an embodiment, the delivery vehicle is selected from a lipid particle, a sugar particle, a metal particle, a protein particle, a liposome, an exosome, a microvesicle, a gene gun, or a viral vector (such as a replication-defective retrovirus, a lentivirus, an adenovirus, or an adeno-associated virus).

Host Cell

The present disclosure also relates to a cell or cell line or progeny thereof in vitro or in vivo, and the cell or cell line or progeny thereof includes the engineered type V Cas protein, the fusion protein, the nucleic acid, the protein-nucleic acid complex, the activated CRISPR complex, the vector, or the delivery composition of the present disclosure.

In some embodiments, the cell is a prokaryotic cell.

In some embodiments, the cell is a eukaryotic cell. In some embodiments, the cell is a mammalian cell. In some embodiments, the cell is a human cell. In some embodiments, the cell is a non-human mammalian cell, such as a cell of a non-human primate, cow, sheep, pig, dog, monkey, rabbit, or a rodent (such as a rat or mouse). In some embodiments, the cell is a non-mammalian eukaryotic cell, such as a cell of a poultry bird (such as chicken), fish, or crustacea (such as clam or shrimp). In some embodiments, the cell is a plant cell, such as a cell possessed by a monocotyledonous plant or a dicotyledonous plant or a cell possessed by a cultivated plant or a food crop such as *Manihot esculenta, Zea mays, Sorghum bicolor, Glycine max, Triticum aestivum*, oats, or *Oryza sativa*. For example, the cell is a cell possessed by an alga, a tree, a production plant, a fruit, or a vegetable (for example, a tree such as a citrus tree or a nut tree; or a nightshade, cotton, tobacco, tomato, grape, coffee, cocoa, or the like).

In some embodiments, the cell is a stem cell or a stem cell line.

In some cases, the host cell of the present disclosure may include a gene or a genome modification that is not present in a WT of the host cell.

Gene Editing Method and Use

The engineered type V Cas protein, the nucleic acid, the composition, the CRISPR/Cas system, the vector system, the delivery composition, the activated CRISPR complex, or the host cell of the present disclosure can be used in one or more of targeting and/or editing a target nucleic acid; cleaving a double-stranded DNA, a single-stranded DNA, or a single-stranded RNA; non-specifically cleaving and/or degrading a collateral nucleic acid; non-specifically cleaving a single-stranded nucleic acid; nucleic acid detection; detecting a nucleic acid in a target sample; specifically editing a double-stranded nucleic acid; base-editing a double-stranded nucleic acid; and base-editing a single-stranded nucleic acid. In other embodiments, the products of the present disclosure can also be used to prepare a reagent or a kit for one or more of the above purposes.

The present disclosure also provides use of the engineered type V Cas protein, the nucleic acid, the composition, the CIRSPR/Cas system, the vector system, the delivery composition, or the activated CRISPR complex in gene editing, gene targeting, or gene cleaving; or in preparation of a reagent or kit for gene editing, gene targeting, or gene cleaving.

In an embodiment, the gene editing, gene targeting, or gene cleaving refers to gene editing, gene targeting, or gene cleaving inside and/or outside a cell.

The present disclosure also provides a method for editing, targeting, or cleaving a target nucleic acid, including: making the target nucleic acid in contact with the engineered type V Cas protein, the nucleic acid, the composition, the CIRSPR/Cas system, the vector system, the delivery composition, or the activated CRISPR complex. In an embodiment, the method includes: editing, targeting, or cleaving the target nucleic acid inside or outside a cell.

The gene editing or the editing a target nucleic acid includes modifying a gene, knocking out a gene, changing expression of a gene product, repairing a mutation, and/or inserting a polynucleotide or a gene mutation.

The editing can be conducted in a prokaryotic cell and/or a eukaryotic cell.

In an eighth aspect, the present disclosure also provides use of the engineered type V Cas protein, the nucleic acid, the composition, the CIRSPR/Cas system, the vector system, the delivery composition, or the activated CRISPR complex in nucleic acid detection; or in preparation of a reagent or kit for nucleic acid detection.

In a ninth aspect, the present disclosure also provides a method for cleaving a single-stranded nucleic acid, including: making a nucleic acid group in contact with the engineered type V Cas protein and the gRNA, where the nucleic acid group includes a target nucleic acid and a plurality of non-target single-stranded nucleic acids, and the engineered type V Cas protein cleaves the plurality of non-target single-stranded nucleic acids.

The gRNA can bind to the Cas protein.

The gRNA can target the target nucleic acid.

The contact can be allowed inside a cell in vitro or in vivo.

Preferably, the cleaving a single-stranded nucleic acid refers to non-specific cleaving.

In a tenth aspect, the present disclosure also provides use of the engineered type V Cas protein, the nucleic acid, the composition, the CIRSPR/Cas system, the vector system, the delivery composition, or the activated CRISPR complex in non-specific cleavage of a single-stranded nucleic acid; or in preparation of a reagent or kit for non-specific cleavage of a single-stranded nucleic acid.

In an eleventh aspect, the present disclosure also provides a kit for gene editing, gene targeting, or gene cleaving, including the engineered type V Cas protein, the gRNA, the nucleic acid, the composition, the CIRSPR/Cas system, the vector system, the delivery composition, the activated CRISPR complex, or the host cell.

In a twelfth aspect, the present disclosure also provides a kit for detecting a target nucleic acid in a sample, including: (a) the engineered type V Cas protein or a nucleic acid encoding the Cas protein; (b) the gRNA, or a nucleic acid encoding the gRNA, or a precursor RNA including the gRNA, or a nucleic acid encoding the precursor RNA; and (c) a single-stranded nucleic acid detector that does not hybridize with the gRNA.

It is known in the art that the precursor RNA can be cleaved or processed into the above-mentioned mature gRNA.

In a thirteenth aspect, the present disclosure provides use of the engineered type V Cas protein, the nucleic acid, the composition, the CIRSPR/Cas system, the vector system, the delivery composition, the activated CRISPR complex, or the host cell in preparation of a formulation or a kit, where the formulation or the kit is used for:

(i) gene or genome editing;
(ii) target nucleic acid detection and/or diagnosis;
(iii) editing a target sequence in a target gene locus to modify an organism or a non-human organism;
(iv) disease treatment; and
(v) targeting a target gene.

Preferably, the gene or genome editing is conducted inside or outside a cell.

Preferably, the target nucleic acid detection and/or diagnosis refer(s) to target nucleic acid detection and/or diagnosis in vitro.

Preferably, the disease treatment refers to treatment of a disease caused by a defect of a target sequence in a target gene locus.

In a fourteenth aspect, the present disclosure provides a method for detecting a target nucleic acid in a sample, including: making the sample in contact with the engineered type V Cas protein, a gRNA, and a single-stranded nucleic acid detector; and detecting a detectable signal generated due to cleavage of the Cas protein on the single-stranded nucleic acid detector to detect the target nucleic acid, where the gRNA includes a region to bind to the Cas protein and a guide sequence to hybridize with the target nucleic acid, and the single-stranded nucleic acid detector does not hybridize with the gRNA.

Method for Specifically Modifying a Target Nucleic Acid

In a fifteenth aspect, the present disclosure also provides a method for specifically modifying a target nucleic acid, including: making the target nucleic acid in contact with the engineered type V Cas protein, the nucleic acid, the composition, the CIRSPR/Cas system, the vector system, the delivery composition, or the activated CRISPR complex.

The specific modification may occur in vivo or in vitro.

The specific modification may occur inside or outside a cell.

In some cases, the cell may be selected from a prokaryotic cell or a eukaryotic cell, such as an animal cell, a plant cell, or a microbial cell.

In an embodiment, the modification refers to a break in the target sequence, such as a single-strand break/double-strand break in DNA or a single-strand break in RNA.

In some cases, the method may further include making the target nucleic acid in contact with a donor polynucleotide, where the donor polynucleotide, a portion of the donor polynucleotide, a copy of the donor polynucleotide, or a portion of the copy of the donor polynucleotide is integrated into the target nucleic acid.

In an embodiment, the modification may further include inserting an edit template (such as an exogenous nucleic acid) into the break.

In an embodiment, the method may further include making an edit template in contact with the target nucleic acid or delivering the edit template to a cell with the target nucleic acid. In an embodiment, the method may repair the broken target gene through homologous recombination with an exogenous template polynucleotide. In some embodiments, the repair may cause a mutation, including insertion, deletion, or substitution of one or more nucleotides in the target gene. In other embodiments, the mutation may cause one or more amino acid changes in a protein expressed by a gene carrying the target sequence.

Detection (Non-Specific Cleavage)

In a sixteenth aspect, the present disclosure provides a method for detecting a target nucleic acid in a sample, including: making the sample in contact with the engineered type V Cas protein, the nucleic acid, the composition, the CIRSPR/Cas system, the vector system, the delivery composition, or the activated CRISPR complex and the single-stranded nucleic acid detector; and detecting a detectable signal generated due to cleavage of the Cas protein on the single-stranded nucleic acid detector to detect the target nucleic acid.

In the present disclosure, the target nucleic acid includes ribonucleotides or deoxyribonucleotides; and the target nucleic acid includes a single-stranded nucleic acid and a double-stranded nucleic acid, such as single-stranded DNA, double-stranded DNA, single-stranded RNA, and double-stranded RNA.

In an embodiment, the target nucleic acid is derived from a sample such as a virus, a bacterium, a microorganism, a soil, a water source, a human body, an animal, and a plant. Preferably, the target nucleic acid is a product of enrichment or amplification by a method such as PCR, NASBA, RPA, SDA, LAMP, HAD, NEAR, MDA, RCA, LCR, or RAM.

In an embodiment, the target nucleic acid is a viral nucleic acid, a bacterial nucleic acid, a disease-related specific nucleic acid such as a specific mutation site or a single nucleotide polymorphism (SNP) site, or a nucleic acid different from a control; preferably, the virus is a plant virus or an animal virus, such as papilloma virus, liver DNA virus, herpes virus, adenovirus, poxvirus, parvovirus, and coronavirus; and preferably, the virus is a coronavirus, such as SARS, SARS-CoV2 (COVID-19), HCoV-229E, HCoV-OC43, HCoV-NL63, HCoV-HKU1, and Mers-Cov.

In the present disclosure, the gRNA and the target sequence on the target nucleic acid have a matching degree of at least 50%, preferably at least 60%, preferably at least 70%, preferably at least 80%, and preferably at least 90%.

In an embodiment, when the target sequence includes one or more characteristic sites (such as specific mutation sites or SNPs), the characteristic sites completely match the gRNA.

In an embodiment, the detection method may include one or more gRNAs with different guide sequences, which target different target sequences.

In the present disclosure, the single-stranded nucleic acid detector includes, but is not limited to, a single-stranded DNA, a single-stranded RNA, a DNA-RNA hybrid, a nucleic acid analogue, a base modifier, and a single-stranded nucleic acid detector with an abasic spacer; and the nucleic acid analogue includes, but is not limited to, locked nucleic acid, bridged nucleic acid, morpholino, glycol nucleic acid, hexitol nucleic acid, threose nucleic acid, arabinose nucleic acid, 2'-O-methyl RNA, 2'-methoxyacetyl RNA, 2'-fluoro RNA, 2'-amino RNA, 4'-thio RNA, and a combination thereof, including optional ribonucleotide or deoxyribonucleotide residues.

In the present disclosure, the detectable signal is detected in the following ways: vision-based detection, sensor-based detection, color detection, fluorescence signal-based detection, gold nanoparticle-based detection, fluorescence polarization, colloidal phase change/dispersion, electrochemical detection, and semiconductor-based detection.

In the present disclosure, preferably, two termini of the single-stranded nucleic acid detector are provided with a fluorophore and a quencher, respectively; and when the single-stranded nucleic acid detector is cleaved, a detectable fluorescence signal can be presented. The fluorophore is selected from one or more of FAM, FITC, VIC, JOE, TET, CY3, CY5, ROX, Texas Red, or LC RED460; and the quencher is selected from one or more of BHQ1, BHQ2, BHQ3, Dabcyl, or Tamra.

In other embodiments, a 5' terminus and a 3' terminus of the single-stranded nucleic acid detector are provided with different labeling molecules, respectively. The single-stranded nucleic acid detector is subjected to a colloidal gold test before and after being cleaved by the Cas protein; and the single-stranded nucleic acid detector shows different chromogenic results on the colloidal gold detection line and control line before and after being cleaved by the Cas protein.

In some embodiments, the method for detecting a target nucleic acid may further include: comparing a level of the detectable signal with a reference signal level, and determining an amount of the target nucleic acid in the sample based on the level of the detectable signal.

In some embodiments, the method for detecting a target nucleic acid may also include: using a RNA reporter nucleic acid and a DNA reporter nucleic acid (such as a fluorescence color) on different channels, measuring a signal level of the RNA and DNA reporter molecules and an amount of the target nucleic acid in the RNA and DNA reporters to determine a level of the detectable signal, and sampling based on a combined (such as minimum or product) level of the detectable signal.

In an embodiment, the target gene is present in a cell.

In an embodiment, the cell is a prokaryotic cell.

In an embodiment, the cell is a eukaryotic cell.

In an embodiment, the cell is an animal cell.

In an embodiment, the cell is a human cell.

In an embodiment, the cell is a plant cell, such as a cell possessed by a cultivated plant (such as *Manihot esculenta*,

*Zea mays, Sorghum bicolor, Triticum aestivum,* or *Oryza sativa*), an alga, a tree, or a vegetable.

In an embodiment, the target gene is present in a nucleic acid in vitro (such as a plasmid).

In an embodiment, the target gene is present in a plasmid.

HNH Domain and Use Thereof

In a seventeenth aspect, the present disclosure also provides an HNH domain.

In an embodiment, the HNH domain is selected from one or more of an HNH domain derived from Cas9, an HNH domain derived from Mbps, an HNH domain derived from Mbvp, an HNH domain derived from *Arabidopsis thaliana*, an HNH domain derived from *Papaver somniferum*, an HNH domain derived from *Glycine max*, an HNH domain derived from *Chelonia mydas*, and an HNH domain derived from Halovirus.

In an embodiment, an amino acid sequence of the HNH domain has at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or at least 100% sequence identity with SEQ ID NOS: 1-8, and has a biological function of the HNH domain.

In an embodiment, an amino acid sequence of the HNH domain is obtained through substitution, deletion, or addition of one or more amino acids based on SEQ ID NOS: 1-8, for example, substitution, deletion, or addition of 1 to 20 amino acids, such as substitution, deletion, or addition of 1, 2, 3, 4, 5, 6, 7, 8, 9, 10, 11, 12, 13, 14, 15, 16, 17, 18, 19, or 20 amino acids; and the amino acid sequence of the HNH domain has a biological function of the HNH domain.

The present disclosure also provides use of the HNH domain in improvement of an editing efficiency of a Cas protein.

The present disclosure also provides use of the HNH domain in preparation of a Cas protein with an improved editing efficiency.

In an embodiment, the Cas protein is a type V Cas protein; and preferably, the type V Cas protein is selected from one or more of Cas12i, Cas12j, Cas12a, Cas12b, Cas12d, Cas12e, Cas12f, Cas12g, Cas12h, and Cas-sf0005. In an embodiment, the type V Cas protein is a Cas protein of the Cas12i family, such as Cas12i1, Cas12i2, Cas12i3, or Cas12i12. In an embodiment, the type V Cas protein is Cas12a, such as FnCas12a, AsCas12a, LbCas12a, Lb5Cas12a, HkCas12a, OsCas12a, TsCas12a, BbCas12a, BoCas12a, or Lb4Cas12a, and is preferably LbCas12a. In an embodiment, the type V Cas protein is Cas-sf0005. In an embodiment, the type V Cas protein is a Cas protein of the Cas12j family, such as Cas12j19.

In an embodiment, the HNH domain is located between two continuous or non-continuous amino acids of the Cas protein to improve an editing efficiency of the Cas protein.

In an embodiment, an amino acid sequence of the Cas protein has at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with SEQ ID NO: 9, SEQ ID NO: 19, SEQ ID NO: 10, or SEQ ID NO: 11.

In an embodiment, an amino acid sequence of the Cas protein is obtained through substitution, deletion, or addition of one or more amino acids based on SEQ ID NO: 9, SEQ ID NO: 19, SEQ ID NO: 10, or SEQ ID NO: 11, for example, substitution, deletion, or addition of 1 to 20 amino acids, such as substitution, deletion, or addition of 1, 2, 3, 4, 5, 6, 7, 8, 9, 10, 11, 12, 13, 14, 15, 16, 17, 18, 19, or 20 amino acids.

In an embodiment, the two continuous or non-continuous amino acids of the Cas protein are a first amino acid and a second amino acid, respectively, and the HNH domain is located between the first amino acid and the second amino acid.

In an embodiment, the HNH domain is located at an N-terminus of the Cas protein.

In an embodiment, the HNH domain is located between two continuous or non-continuous amino acids of the Cas protein, where the two continuous or non-continuous amino acids of the Cas protein are a first amino acid and a second amino acid, respectively, the HNH domain is located between the first amino acid and the second amino acid, the first amino acid and the second amino acid are selected from any one of amino acid positions corresponding to amino acids 1 to 10 (an amino acid 1, 2, 3, 4, 5, 6, 7, 8, 9, or 10) at the N-terminus of the Cas protein, and the first amino acid and the second amino acid are different amino acid positions of the Cas protein.

In an embodiment, the first amino acid is selected from any one of amino acid positions corresponding to amino acids 1 to 10 (an amino acid 1, 2, 3, 4, 5, 6, 7, 8, 9, or 10) of SEQ ID NO: 9, the second amino acid is selected from any one of amino acid positions corresponding to amino acids 1 to 10 (an amino acid 1, 2, 3, 4, 5, 6, 7, 8, 9, or 10) of SEQ ID NO: 9, and the first amino acid and the second amino acid are different amino acid positions corresponding to SEQ ID NO: 9.

In an embodiment, the first amino acid is selected from any one of amino acid positions corresponding to amino acids 1 to 10 (an amino acid 1, 2, 3, 4, 5, 6, 7, 8, 9, or 10) of SEQ ID NO: 19, the second amino acid is selected from any one of amino acid positions corresponding to amino acids 1 to 10 (an amino acid 1, 2, 3, 4, 5, 6, 7, 8, 9, or 10) of SEQ ID NO: 19, and the first amino acid and the second amino acid are different amino acid positions corresponding to SEQ ID NO: 19.

In an embodiment, the first amino acid and the second amino acid are selected from amino acids 1 and 2 of an amino acid sequence shown in SEQ ID NO: 10.

In an embodiment, the first amino acid and the second amino acid are selected from amino acids 1 and 2 of an amino acid sequence shown in SEQ ID NO: 11.

In an embodiment, the first amino acid and the second amino acid are selected from amino acid positions corresponding to amino acids 794 and 795 of SEQ ID NO: 9.

Terms and Definitions

In the present disclosure, unless otherwise specified, the scientific and technical terms used herein have the meanings commonly understood by those skilled in the art. In addition, the molecular genetics, nucleic acid chemistry, chemistry, molecular biology, biochemistry, cell culture, microbiology, cell biology, genomics, and recombinant DNA operation procedures used herein are routine procedures widely used in the corresponding fields. Moreover, in order to well explain the present disclosure, definitions and explanations of related terms are provided below.

The nucleic acid cleavage or the cleavage of a nucleic acid herein includes: a DNA or RNA break in a target nucleic acid caused by the engineered type V Cas protein described herein (Cis cleavage), and a DNA or RNA break in a collateral nucleic acid substrate (single-stranded nucleic acid substrate) (namely, non-specific or non-targeting Trans cleavage). In some embodiments, the cleavage refers to a double-stranded DNA break. In some embodiments, the cleavage refers to a single-stranded DNA break or a single-stranded RNA break.

CRISPR System

The terms "CRISPR-Cas system" and "CRISPR system" used herein can be used interchangeably and have the meaning commonly understood by those skilled in the art, and a CRISPR-Cas system or a CRISPR system usually includes a transcription product or other elements related to the expression of a Cas gene, or a transcription product or other elements capable of guiding an activity of the Cas gene.

CRISPR/Cas Complex

As used herein, the term "CRISPR/Cas complex" refers to a complex produced through binding of a gRNA or mature crRNA to the Cas protein, and a CRISPR/Cas complex includes a direct repeat that hybridizes with a guide sequence of the target sequence and binds to the Cas protein. The CRISPR/Cas complex can recognize and cleave a polynucleotide capable of hybridizing with the gRNA or mature crRNA.

gRNA

As used herein, the terms "gRNA", "mature crRNA", and "guide sequence" can be used interchangeably and have the meaning commonly understood by those skilled in the art. Generally, a gRNA can include a direct repeat and a guide sequence, or is essentially composed of or is composed a direct repeat and a guide sequence.

In some cases, the guide sequence can be any polynucleotide sequence that shows sufficient complementarity with a target sequence to hybridize with the target sequence and guide the specific binding of the CRISPR/Cas complex to the target sequence. In an embodiment, under optimal alignment, a complementarity degree between the guide sequence and a corresponding target sequence is at least 50%, at least 60%, at least 70%, at least 80%, at least 90%, at least 95%, or at least 99%. Determining the optimal alignment is within the competence of those of ordinary skill in the art. For example, there are published and commercially-available alignment algorithms and programs, including but not limited to Smith-Waterman, Bowtie, Geneious, Biopython, and SeqMan in ClustalW and matlab.

Target Sequence

A target sequence refers to a polynucleotide targeted by a guide sequence in gRNA, such as a sequence that has complementarity with the guide sequence, where the hybridization between the target sequence and the guide sequence will promote the production of a CRISPR/Cas complex (including a Cas protein and a gRNA). Complete complementarity is not necessary, as long as there is sufficient complementarity to cause hybridization and promote the production of a CRISPR/Cas complex.

The target sequence can include any polynucleotide, such as DNA or RNA. In some cases, the target sequence is located inside or outside a cell. In some cases, the target sequence is located in a nucleus or cytoplasm of a cell. In some cases, the target sequence may be located in an organelle such as a mitochondrion or a chloroplast of a eukaryotic cell. A sequence or a template that can be recombined into a target gene locus with the target sequence is called an edit template, edit polynucleotide, or edit sequence. In an embodiment, the edit template is an exogenous nucleic acid. In an embodiment, the recombination refers to homologous recombination.

In the present disclosure, the target sequence, target polynucleotide, or target nucleic acid can be any endogenous or exogenous polynucleotide for a cell (such as a eukaryotic cell). For example, the target polynucleotide may be a polynucleotide present in a nucleus of a eukaryotic cell.

The target polynucleotide may be a sequence encoding a gene product (such as a protein) or a non-coding sequence (such as a regulatory polynucleotide or useless DNA). In some cases, the target sequence should be related to a protospacer adjacent motif (PAM).

Single-Stranded Nucleic Acid Detector

The single-stranded nucleic acid detector of the present disclosure refers to a sequence with 2 to 200 nucleotides, preferably 2 to 150 nucleotides, preferably 3 to 100 nucleotides, preferably 3 to 30 nucleotides, preferably 4 to 20 nucleotides, and preferably 5 to 15 nucleotides. Preferably, the single-stranded nucleic acid detector is a single-stranded DNA molecule, a single-stranded RNA molecule, or a single-stranded DNA-RNA hybrid.

Two termini of the single-stranded nucleic acid detector include different reporter groups or labeling molecules. When the single-stranded nucleic acid detector is in an initial state (that is, when the single-stranded nucleic acid detector is not cleaved), no reporter signal is presented; and when the single-stranded nucleic acid detector is cleaved, a detectable signal is presented, indicating a detectable difference before and after cleavage.

In an embodiment, the reporter groups or labeling molecules include fluorophores and quenchers. The fluorophores are selected from one or more of FAM, FITC, VIC, JOE, TET, CY3, CY5, ROX, Texas Red, or LC RED460; and the quenchers are selected from one or more of BHQ1, BHQ2, BHQ3, Dabcyl, or Tamra.

In an embodiment, the single-stranded nucleic acid detector has a first molecule (such as FAM or FITC) linked to a 5' terminus and a second molecule (such as biotin) linked to a 3' terminus. A reaction system with the single-stranded nucleic acid detector may be used in combination with a flow strip to detect a target nucleic acid (preferably, colloidal gold detection). The flow strip is designed to have two capture lines, where an antibody to bind to a first molecule (namely, an anti-first molecule antibody) is arranged at a sample contact end (colloidal gold), an antibody to bind to the anti-first molecule antibody is arranged at a first line (control line), and an antibody to bind to a second molecule (namely, an anti-second molecule antibody, such as avidin) is arranged at a second line (test line). As a reaction proceeds along the strip, the anti-first molecule antibody binds to the first molecule and carries a cleaved or uncleaved oligonucleotide to a capture line, where a cleaved reporter will bind to the antibody binding to the anti-first molecule antibody at a first capture line; and an uncleaved reporter will bind to the anti-second molecule antibody at a second capture line. The binding of a reporter group to each line will cause a strong readout/signal (such as a color). The more the reporters cleaved, the more the signals accumulating at the first capture line, and the fewer the signals occurring at the second capture line. In some aspects, the present disclosure relates to use of the flow strip as described herein in detection of a nucleic acid. In some aspects, the present disclosure relates to a method for detecting a nucleic acid using the flow strip as defined herein, such as a (lateral) flow test or a (lateral) flow immunochromatographic assay. In some aspects, the molecules in the single-stranded nucleic acid detector can be used instead of each other, or positions of the molecules can be changed. As long as a reporting principle is the same as or similar to that of the present disclosure, an improved method is also included in the present disclosure.

The detection method of the present disclosure can be used for quantitative detection of a target nucleic acid to be detected. An index for the quantitative detection can be quantified according to a signal intensity of a reporter group, for example, according to a luminous intensity of a fluorophore or according to a width of a chromogenic band.

WT

As used herein, the term "WT" has the meaning commonly understood by those skilled in the art, and indicates the typical form of an organism, a strain, or a gene, or a characteristic to distinguish the organism, strain, or gene in nature from a mutant or variant form thereof, which can be isolated from a natural source and is not artificially modified intentionally.

Derivatization

As used herein, the term "derivatization" refers to a chemical modification to an amino acid, a polypeptide, or a protein, where one or more substituents have been covalently linked to the amino acid, the polypeptide, or the protein. The substituents can also be referred to as side chains.

A derivatized protein is a derivative of a protein. Generally, the derivatization of a protein will not adversely affect a desired activity of the protein (for example, an activity to bind to gRNA, an endonuclease activity, and an activity to bind to a specific position of a target sequence and cleave the target sequence under the guidance of a gRNA). That is, a derivative of a protein has the same activity as the protein.

Derivatized Protein

A derivatized protein, also known as a protein derivative, refers to a modified form of a protein, for example, one or more amino acids of the protein can be deleted, inserted, modified, and/or substituted.

Non-Natural

As used herein, the terms "non-natural" and "engineered" can be used interchangeably and refer to manual intervention. When these terms are used to describe a nucleic acid or a polypeptide, it means that the nucleic acid or polypeptide is at least substantially isolated from a natural source or separated from at least another component binding to the nucleic acid or polypeptide in the nature.

Orthologue, Ortholog

As used herein, the term "orthologue, ortholog" has the meaning commonly understood by those skilled in the art. As a further guide, an orthologue of a protein described herein refers to a protein of a different species, which implements the same function as or the similar function to the protein.

Identity

As used herein, the term "identity" refers to the sequence matching between two polypeptides or between two nucleic acids. When specified positions in two sequences to be compared are occupied by the same base or amino acid monomer subunit (for example, a specified position in each of two DNA molecules is occupied by adenine, or a specified position in each of two peptides is occupied by lysine), the molecules are identical at the position. The "identity" between two sequences is a function of the number of matched positions shared by the two sequences/the number of compared positions×100. For example, if 6 of 10 positions in a sequence match corresponding positions in another sequence, then the two sequences have 60% identity. For example, DNA sequences CTGACT and CAGGTT have 50% identity (3 of 6 positions are matching). Generally, the comparison is conducted when two sequences are aligned to produce maximum identity. Such alignment can be allowed by using, for example, a method of Needleman et. al. (1970) J. Mol. Biol. 48: 443-453 that can be conveniently implemented by a computer program such as Align program (DNAstar, Inc.). The identity between two amino acid sequences can also be determined by using an algorithm of E. Meyers and W. Miller (Comput. Appl Biosci., 4:11-17 (1988) integrated into the ALIGN program (version 2.0), a PAM120 weight residue table, a gap length penalty of 12, and a gap length penalty of 4. In addition, the identity between two amino acid sequences can be determined by using Needleman and Wunsch (J MoI Biol. 48: 444-453 (1970)) algorithms in the GAP program integrated into the GCG software package (available on the world wide web at gcg.com), a Blossum 62 matrix or a PAM250 matrix, a gap weight of 16, 14, 12, 10, 8, 6, or 4, and a length weight of 1, 2, 3, 4, 5, or 6.

Vector

The term "vector" refers to a nucleic acid that can deliver another nucleic acid linked thereto. The vector includes, but is not limited to, a single-stranded, double-stranded, or partially double-stranded nucleic acid; a nucleic acid with one or more free ends or without free ends (such as circular); DNA, RNA, or a nucleic acid of both; and other diverse polynucleotides known in the art. The vector can be introduced into a host cell through transformation, transduction, or transfection, such that a genetic material element carried by the vector can be expressed in the host cell. A vector can be introduced into a host cell to produce a transcript, a protein, or a peptide, including the protein, the fusion protein, the isolated nucleic acid, and the like (for example, a CRISPR transcript, such as a nucleic acid transcript, a protein, or an enzyme) described herein. A vector may include a variety of elements to control the expression, including but not limited to a promoter sequence, a transcription initiation sequence, an enhancer sequence, a selection element, and a reporter gene. In addition, the vector may also include a replication origin.

A type of a vector is a plasmid, which refers to a circular double-stranded DNA loop where an additional DNA fragment can be inserted, for example, by a standard molecular cloning technique.

Another type of a vector is a viral vector in which a virus-derived DNA or RNA sequence is present in a vector for packaging a virus (such as a retrovirus, a replication-defective retrovirus, an adenovirus, a replication-defective adenovirus, and an adeno-associated virus). A viral vector also includes a polynucleotide carried by a virus to be transfected into a host cell. Some vectors (for example, bacterial vectors with a bacterial replication origin and episomal mammalian vectors) can autonomously replicate in a host cell into which the vectors are introduced.

Other vectors (such as non-episomal mammalian vectors) will be integrated into a genome of a host cell and thus replicate with the genome of the host cell after being introduced into the host cell. Moreover, some vectors can guide the expression of genes operably linked thereto. Such vectors are referred to as expression vectors herein.

Host Cell

As used herein, the term "host cell" refers to a cell that can be introduced with a vector, including, but not limited to, a prokaryotic cell such as *Escherichia coli* or *Bacillus subtilis*, and a eukaryotic cell such as a microbial cell, a fungal cell, an animal cell, and a plant cell.

Those skilled in the art will understand that the design of an expression vector may depend on factors such as selection of a host cell to be transformed, and a desired expression level.

Regulatory Element

As used herein, the term "regulatory element" is intended to include a promoter, an enhancer, an IRES, and other expression control elements (for example, a transcriptional termination signal, such as a polyadenylation signal and a poly-U sequence), and the detailed description can be seen in Goeddel, "*GENE EXPRESSION TECHNOLOGY:METHODS IN ENZYMOLOGY*" 185, Academic Press, San Diego, California (1990). In some cases, the regulatory element includes sequences that guide the constitutive expression of a nucleotide sequence in many types of host cells and sequences that guide the expression of the nucleotide sequence only in some host cells (such as a tissue-specific regulatory sequence). A tissue-specific promoter can mainly guide the expression in a desired tissue of interest, such as muscles, neurons, bones, skin, blood, specific organs (such as liver and pancreas), or specific cell types (such as lymphocytes). In some cases, a regulatory element can also guide the expression in a time-dependent manner (such as in a cell cycle-dependent or developmental stage-dependent manner), which may be or may not be tissue or cell type-specific. In some cases, the term "regulatory element" covers enhancer elements, such as WPRE; a CMV enhancer; an R-U5' fragment in LTR of HTLV-I ((Mol.Cell.Biol., Vol 8 (1): 466-472, 1988); an SV40 enhancer; and an intron sequence between exons 2 and 3 of rabbit 3-globin (Proc. Natl. Acad. Sci. USA., Vol. 78 (3): 1527-31, 1981).

Promoter

As used herein, the term "promoter" has the meaning well known to those skilled in the art, and refers to a non-coding nucleotide sequence located upstream of a gene and capable of promoting the expression of a downstream gene. A constitutive promoter is a nucleotide sequence that will cause the generation of a gene product in a cell under most or all physiological conditions of the cell after the promoter is operably linked to a polynucleotide encoding or defining the gene product. An inducible promoter is a nucleotide sequence that will cause the generation of a gene product in a cell only when there is an inducer corresponding to the promoter in the cell after the promoter is operably linked to a polynucleotide encoding or defining the gene product. A tissue-specific promoter is a nucleotide sequence that will cause the generation of a gene product in a cell basically only when the cell is a cell of the tissue type corresponding to the promoter after the promoter is operably linked to a polynucleotide encoding or defining a gene product.

NLS

"NLS" is an amino acid sequence that tags a protein for import into a nucleus through nuclear transport, that is, a protein with NLS is transported to the nucleus. Typically, NLS may include positively-charged Lys or Arg residues that are exposed on a surface of a protein. Exemplary NLS includes, but is not limited to, SV40 large T antigen, EGL-13, c-Myc, and TUS protein. In some embodiments, the NLS includes a PKKKRKV (SEQ ID NO: 21) sequence. In some embodiments, the NLS includes an AVKRPAATKKAGQAKKKKLD (SEQ ID NO: 22) sequence. In some embodiments, the NLS includes a PAAKRVKLD (SEQ ID NO: 23) sequence. In some embodiments, the NLS includes an MSRRRKANPTKLSENAKKLAKEVEN (SEQ ID NO: 24) sequence. In some embodiments, the NLS includes a KLKIKRPVK (SEQ ID NO: 25) sequence. Other NLS includes, but is not limited to, an acidic M9 domain of hnRNP A1, and sequences KIPIK (SEQ ID NO: 26) and PY-NLS in a yeast transcription repressor Mata2.

Operably Linked

As used herein, the term "operably linked" means that a nucleotide sequence of interest is linked to one or more regulatory elements in a manner that allows the expression of the nucleotide sequence (for example, in an in vitro transcription/translation system or in a host cell when the vector is introduced into the host cell).

Complementarity

As used herein, the term "complementarity" refers to an ability of a nucleic acid to form one or more hydrogen bonds with another nucleic acid by means of traditional Watson-Crick or another non-traditional form. The complementarity percentage refers to a percentage of residues in a first nucleic acid that can form hydrogen bonds (such as Watson-Crick base pairing) with a second nucleic acid (such as 5, 6, 7, 8, 9, and 10 of 10, namely 50%, 60%, 70%, 80%, 90%, and 100% complementarity). "Completely complementary" means that all continuous residues of a first nucleic acid sequence form hydrogen bonds with the same number of continuous residues in a second nucleic acid sequence. As used herein, "substantially complementary" means that there is at least 60%, 65%, 70%, 75%, 80%, 85%, 90%, 95%, 97%, 98%, 99%, or 100% complementarity in a region with 8, 9, 10, 11, 12, 13, 14, 15, 16, 17, 18, 19, 20, 21, 22, 23, 24, 25, 30, 35, 40, 45, 50, or more nucleotides, or means that two nucleic acids can hybridize under stringent conditions.

Stringent Conditions

As used herein, "stringent conditions" for hybridization refer to conditions under which a nucleic acid showing complementarity with a target sequence mainly hybridizes with the target sequence and substantially does not hybridize with a non-target sequence. Stringent conditions are usually sequence-dependent and vary depending on many factors. Generally, the longer the sequence, the higher the temperature at which the sequence specifically hybridizes with a corresponding target sequence.

Hybridization

The term "hybridization" or "complementary" or "substantially complementary" means that a nucleic acid (such as RNA and DNA) includes a nucleotide sequence that enables its non-covalent binding, that is, the nucleic acid can form base pairs and/or G/U base pairs with another nucleic acid in a sequence-specific, anti-parallel manner (that is, the nucleic acid specifically binds to a complementary nucleic acid), "annealing" or "hybridizing".

The hybridization requires that two nucleic acids include complementary sequences, but there may be mismatches between bases. Suitable conditions for hybridization between two nucleic acids depend on a length and complementarity degree of the nucleic acids, which are variables well known in the art. Typically, a hybridizable nucleic acid may include 8 or more nucleotides (such as 10 or more nucleotides, 12 or more nucleotides, 15 or more nucleotides, 20 or more nucleotides, 22 or more nucleotides, 25 or more nucleotides, or 30 or more nucleotides).

It should be understood that a sequence of a polynucleotide does not need to be 100% complementary to a sequence of its target nucleic acid for specific hybridization. A polynucleotide may have 60% or more, 65% or more, 70% or more, 75% or more, 80% or more, 85% or more, 90% or more, 95% or more, 98% or more, 99% or more, 99.5% or more, or 100% complementarity with a sequence of a target region in a target nucleic acid sequence to hybridize with the polynucleotide.

The hybridization of a target sequence with a gRNA means that the target sequence and a nucleic acid sequence of the gRNA have at least 60%, 70%, 75%, 80%, 85%, 90%, 91%, 92%, 93%, 94%, 95%, 96%, 97%, 98%, 99%, or 100% complementarity, and thus can be hybridized to produce a complex; or means that at least 12, 15, 16, 17, 18, 19, 20, 21, 22, or more bases in the target sequence are complementary to and paired with that in the nucleic acid sequence of the gRNA, and thus the two sequences can be hybridized to produce a complex.

Expression

As used herein, the term "expression" refers to a process by which a DNA template is transcribed into a polynucleotide (such as mRNA or another RNA transcript) and/or a process by which the transcribed mRNA is subsequently translated into a peptide, a polypeptide, or a protein.

The transcript and the encoded polypeptide can be collectively referred to as a "gene product". If a polynucleotide is derived from genomic DNA (gDNA), the expression can include splicing of mRNA in a eukaryotic cell.

Linker

As used herein, the term "linker" refers to a linear polypeptide produced by linking a plurality of amino acid residues through peptide bonds. The linker of the present disclosure may be an artificially-synthesized amino acid sequence, or a natural polypeptide sequence, such as a polypeptide with a hinge domain function. Such linker polypeptides are well known in the art (see, for example, Holliger, P. et al. (1993) Proc. Natl. Acad. Sci. USA 90: 6444-6448; and Poljak, R. J. et al. (1994) Structure 2: 1121-1123).

Treatment

As used herein, the term "treatment" refers to treating or curing a disease, delaying the onset of symptoms of a disease, and/or delaying the development of a disease.

Subject

As used herein, the term "subject" includes, but is not limited to, various animals, plants, and microorganisms.

Animal

For example, the animal may be a mammal, such as bovine, equine, sheep, swine, canine, feline, leporid, rodent (such as mouse or rat), non-human primate (such as macaque or cynomolgus monkey), or human. In some embodiments, the subject (such as human) suffers from a disorder (such as a disorder caused by a disease-related gene defect).

Plant

The term "plant" should be understood as any differentiated multicellular organism capable of photosynthesis, including: crop plants at a mature or developmental stage, especially monocotyledonous or dicotyledonous plants; vegetable crops including artichoke, turnip cabbage, arugula, leek, asparagus, lettuce (such as head lettuce, leaf lettuce, and romaine lettuce), bok choy, malanga, melons (such as cantaloupe, watermelon, crenshaw melon, honeydew melon, and Roman cantaloupe), rape crops (such as Brussels sprout, cabbage, cauliflower, broccoli, borecole, kale, Chinese cabbage, and bok choy), cardoon, carrot, napa, okra, onion, celery, parsley, chickpea, parsnip, chicory, pepper, *Solanum tuberosum*, gourd (such as marrow squash, cucumber, zucchini, cushaw, and pumpkin), radish, dried ball onion, rutabaga, purple eggplant (also known as eggplant), salsify, lettuce, shallot, endive, garlic, spinach, green onion, cushaw, greens, beets (sugar beets and fodder beets), sweet potato, Swiss chard, wasabi, tomato, turnip, and spices; fruits and/or vine crops such as apple, apricot, cherry, nectarine, peach, pear, plum, prune, cherry, quince, almond, chestnut, hazelnut, pecan, pistachio, walnut, citrus, blueberry, boysenberry, cranberry, currant, loganberry, raspberry, strawberry, blackberry, grape, avocado, banana, kiwi, persimmon, pomegranate, pineapple, tropical fruit, pome, melon, mango, *papaya*, and lychee; field crops, such as clover, alfalfa, evening primrose, meadowfoam, corn/maize (forage corn, sweet corn, and popcorn), *lupulus*, jojoba, peanut, rice, safflower, small grain crops (*Hordeum vulgare*, oat, rye, *Triticum aestivum*, and the like), *Sorghum bicolor, Nicotiana tabacum*, kapok, legumes (beans, lentil, pea, and *Glycine max*), oil plants (canola, leaf mustard, *Papaver somniferum*, olive, sunflower, coconut, castor oil plant, cocoa bean, and groundnut), *Arabidopsis*, fiber plants (cotton, flax, and jute), Lauraceae (cinnamon or camphor), or a plant such as coffee, sugar cane, tea, and natural rubber plants; and/or bedding plants such as a flowering plant, cactus, a succulent plant, and/or an ornamental plant, and trees such as forests (broad-leaved and evergreen trees, such as conifers), fruit trees, ornamental trees, nut-bearing trees, shrubs, and other seedlings.

Advantageous Effects of the Present Disclosure

In the present disclosure, an HNH domain is fused in a type V Cas protein through engineered modification to improve an activity of the type V Cas protein, which has a promising application prospect.

Embodiments of the present disclosure will be described in detail below with reference to accompanying drawings and examples, but those skilled in the art will understand that the following accompanying drawings and examples are only used to illustrate the present disclosure rather than limit the scope of the present disclosure. Through the following detailed description of accompanying drawings and preferred embodiments, various objectives and advantageous aspects of the present disclosure will become apparent to those skilled in the art.

Figure 1:
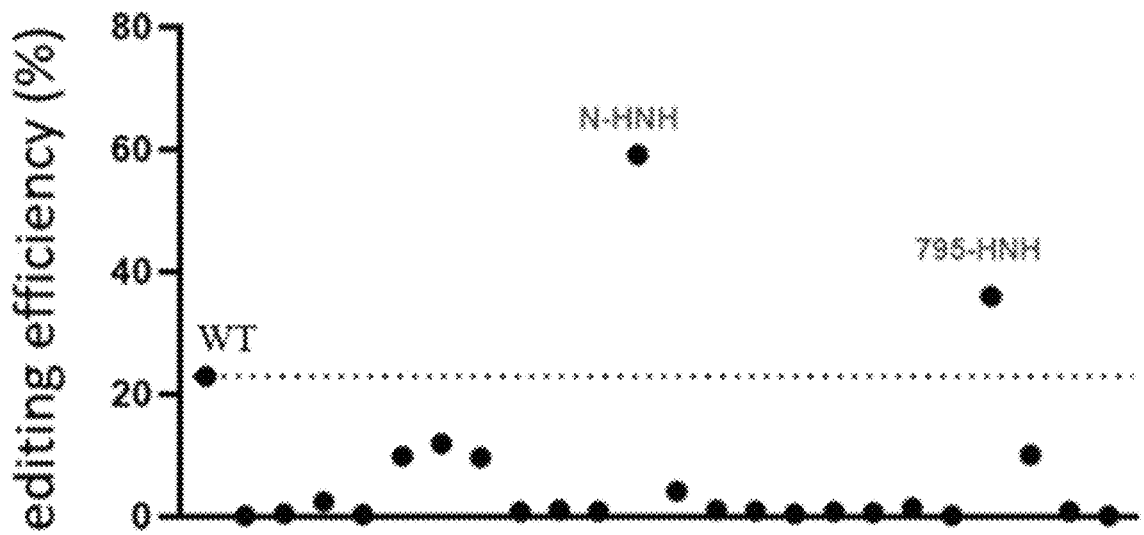
FIG. 1 shows detection results of an editing efficiency of WT Cas12i3 in which an HNH domain is fused.

Sequence information involved in the present disclosure is as follows:

| SEQ ID No: | Sequence abbreviation | Sequence information |
|---|---|---|
| 1 | Sa | liekiklhdmqegkclysleaipledllnnpfnyevdhiiprsvsfdnsfnnkvlvkqeenskkgnrtpfqyl sssdskisyetfkkhilnlakgkgrisktkkeylle |
| 2 | Mbps | gkatdvdhiergddhsrrnlqaacnrchgkkss |
| 3 | Mbvp | cqscghtatpgsgqlhadhiqprsrggtdtldnmrtlckachapks |

| SEQ ID No: | Sequence abbreviation | Sequence information |
|---|---|---|
| 4 | SNF2 | nawhadhiipvyqgggecrlenmrtlcvachad |
| 5 | Ps | nawhadhiipvyrgggecnldnmrtlcvachsdvt |
| 6 | Gm | ckrffncigclcyeydhiipfskggestadncqilqsrvnrlksd |
| 7 | Cm | qfwqvdhikpvysgggqcslenlqtlctvchkerta |
| 8 | HCTV | cascgmtraehkqvygrdlhvhhkipvrvfddvsdahfevnlvtvcmeche |
| 9 | Cas12i3 | mkkvevsrpyqslllpnhrkfkyldetwnayksvksllhrflvcaygavpfnkfvevvekvdndqlvlafa vrlfrlvpvestsfakvdkanlakslanhlpvgtaipanvqsyfdsnfdpkkymwidcaweadrlaremgl sasqfseyattmlwedwlplnkddvngwgsvsglfgegkkedrqqkvkmlnnllngikknppkdytqy lkillnafdakshkeavknykgdstgrtasylseksgeitelmleqlmsniqrdigdkqkeislpkkdvvkk ylesesgvpydqnlwsqayrnaassikktdtrnfnstlekfknevelrgllsegddveilrskffssefhktpd kfvikpehigfnnkynvvaelyklkaeatdfesafatvkdefeekgikhpiknileyiwnnevpvekwgr varfnqseekllrikanptvecnqgmtfgnsamvgevlrsnyvskkgalvsgehggrligqnnmiwlem rllnkgkwethhvpthnmkffeevhaynpsladsvnvrnrlyrsedytqlpssitdglkgnpakllkrqhc alnnmtanvlnpklsftinkknddytviivhsvevskprrevlvgdylvgmdqnqtasntyavmqvvkp kstdaipfrnmwvrfvesgsiesrtlnsrgeyvdqlnhdgvdlfeigdtewvdsarkffnklgvkhkdgtlv dlstaprkayafnnfyfktmlnhlrsnevdltllrneilrvangrfspmrlgslswttlkalgsfkslvlsyfdrlg akemvdkeakdkslfdllvainnkrsnkreertsriasslmtvaqkykvdnavvhvvvegnlsstdrsask ahnrntmdwcsravvkkledmcnlygfnikgvpafytshqdplvhradyddpkpalrcryssysradfs kwgqnalaavvrwasnkkksntcykvgaveflkqhglfadkkltveqflskvkdeeiliprrggrvfltthrll aestfvylngvkyhscnadevaavniclndwvipckkkmkeessasg |
| 10 | Cas12a | msklekftncyslsktlrfkaipvgktqenidnkrllvedekraedykgvkklldryylsfindvlhsiklknl nnyislfrkktrtekenkelenleinlrkeiakafkgnegykslfkkdiietilpeflddkdeialvnsfngftta tgffdnrenmfseeakststsiafrcinenltryisnmdifekvdaifdkhevqeikeilnsdydvedffegeff nfvltqegidvynaiiggfvtesgekikglneyinlynqktkqlplpfkfplykqvlsdreslsfygegytsde evlevfrntlnknseifssikkleklfknfdevyssagifvkngpaistiskdifgewnvirdkwnaeyddihl kkkavvtekyeddrrksfkkigsfsleqlqeyadadlsvveklkeiiiqkvdeiykvygssseklfdadfvlek slkkndavvaimkdlldsvksfenyikaffgegketnrdesfygdfvlaydilllkvdhiydairnyvtqkpy skdkfklyfqnpqfmggwdkdketdyratilrygskyylaimdkkyakclqkidkddvngnyekinyk llpgpnkmlpkvffsskkwmayynpsediqkiykngtfkkgdmfnlndchkldffkdsisrypkwsna ydfnfsetekykdiagfyreveeqgykvsfesaaskkevdklveegklymfqiynkdfsdkshgtpnlhtm yfkllfdennhgqirlsggaelfmrraslkkeelvvhpanspianknpdnpkktttlsydvykdkrfsedqy elhipiainkcpknifkintevrvllkhddnpyvigidrgernllyivvvdgkgniveqyslneiinnfngiri ktdyhslldkkekerfearqnwtsienikelkagyisqvvhkicelvekydavialedlnsgfknsrvkvek qvyqkfekmlidklnymvddkksnpcatggalkgyqitnkfesfksmstqngfifyipawltskidpstgf vnllktkytsiadskkfissfdrimyvpeedlfefaldyknfsrtdadyikkwklysygnririfrnpkknnvf dweevcltsaykelfnkyginyqqgdirallceqsdkafyssfmalmslmlqmrnsitgrtdvdflispvk nsdgifydsrnyeaqenailpknadangayniarkvlwaigqfkkaedekldkvkiaisnkewleyaqts vkh |
| 11 | Cas-sf0005 | mtpktetpvgalikkffpgkrfqknylkdagkklkregeaaaveylsgkqedhpanfcppakvnilaqsrp lsewpinlvskgvqeyvygltaaereangdfgtsrksldrwfartgvpthgyttvqglnlilrhtfnrydgvik kvetrnekrrskatrinvsreadglppieaepeetafgpdgklkerpginpsiycyqqvpvpvpynpakhpal pfsgvdpgaplplgtpnrlsipkgqpgyvpewqrphlstknkrirkwyaranwrrkpgrksvldeaklke aalkeaipiivtigkdwivmdargllravywrgiakpglslkellgffsgdpvldpkrgiatftfklgavavhs rkptrgkkskellilsmtaekphvglvaidlgqtnpvaaefsrvkregetlqaeplgqivlpddlvkdltryrra wdateeqikaeaivqlpeecraevvknqmsaeetkhlildrgvsgdlpwekmtsnttfisdhllakgvtd qvffekkskgkkktgtetvkrkdygwvkllrprlsqetrkavndktwelkrasteyvrlsrrktelarrcvnyi vretkrwtqcedaiaivedlnvrffhgsgerpdgwdnffiskrennwfiqvlhkafsdlalhrglpvieanpar tsitcircrghcdrnnrhgemflclscndlrhadreiatrnltrvavtgemiprriepgeqsgdtkkarsarkgkk aviskreaa |
| 12 | Mbps | mswstsdrssrlpadweenyrqpvlraagyrcqirqrgclgkatdvdhiergddhsrrnlqaacnrchgkk ssaegharkrqlrarrkrpaerhpgrq |
| 13 | Mbvp | mprapkvcrhagcttltttgtcpqhtthrwgnhqgrkvphwlqratfrrdnwtcqscghtatpgsgqlhad hiqprsrggtdtldnmrtlckachapksraeargsnt |
| 14 | SNF2 | mevseeqrrrdeatrlafaekrkqsfdssenpqrqqdfrlakcrkldgsndvcpqegyrnyepvrvlstsvp ekfrvrleicspdsfsvtpvqlqgfrcpeeqeclrqlrkilsdaiplhytqnddggkagvykirdynkvsgclk rsksvevegvpwktlavveklsqsyisgkwqpclpehyteekveqlietlprklvnallpfqldglrfglrrg grcfiademglgktlqaiaiagcfisegsilvvcpavlrftwaeelerwlpsclpsdvhlvfghqdnpaylpr wpkvvvisykmlqhlrttmlerewallivdeshhlrcskkksdppeiktvldvaekvkhiillsgtpsvsrp fdifhqinmlwpgllgdkyefaktycevglvrgiqgkkifqdfskgtrllelnilllnqtvmirrlkqhlltqlpp krrqivtilllkksdialamaivseakkqkdgaiaevtekshepdqnargsneaghvnaensdgpnsdken qlcgklsyqqlgiaklsafrewlslhpllsgldyfpeeidgdrsstkmvvfahhhkvldgiqeficdkgigfvr idgttlprdrqlavqsfqfssevkiaiiigveaggvgldfsaaqnvvflelpktpsllllqaedrahrrgqtsavnv yifcakdtmdesnwqnlnkklhrisstttdgkyd gkteieiggasifkpaeesserevlegqpsesntvvadk ivescddpgtetdvsntidlkddmtsqleilevcpfvengsgsgmrssgtisltmlagenqenhkpknliad dglvkevdsssifplidslrfevsqntgrihlyscipgkdprprphfqnfrpeeieasnpsqgttkeknpesitd dpvhvlailefmkewkslrpiekrkllgkplqlpslselsylsestshnsegllrggskrrntpfseisiplpena |

-continued

| SEQ ID No: | Sequence abbreviation | Sequence information |
|---|---|---|
| | | vwikvnlrsghqrkekeytqawsmsneplcklcqkpcagynakepeyledlfcelacyedyrtrtssryir qelfqiehgictnckldchqlvkrlrplplekrrtyinkaapelfarknllletlvndptegnawhadhiipvyq gggecrlenmrtlcvachadvtaaqcaerklirskarkqlkntlnelrnnpkqkdlsadentketdsatneee delmievpgsaysidqkinhdas |
| 15 | Ps | mmeneawqnilqafmkernglrpvdqkkllrkplqlpltselwylkesinhgseandlmpqgllkggsk qrntplseisqplpanaswkkislcrgrkkekeytqgwtvtgeplcklcqkpckglsktpeyfedlfcema cfqeyrvktsqqslreelfkmehgvcvackldchelvnyirplryvargrehvekvapnlarskklldkliny pregnawhadhiipvyrgggecnldnmrtlcvachsdvtkaqskerrlrnkrgkdrvrdilkglklgssreh nskeqddietrnkededdllmidvpgsdysratdtvtvsnqenqdeae |
| 16 | Gm | msssspqrsrgdgekrprffdsnakaicwskadtvpgrhperwrkdaagnvvckrffncigclcyeydhii pfskggestadncqilqsrvnrlksdkynidsdqlkdyscevnftdkeldiiemavygdvmrpgnqcrcrt iaeklgkfkpkddtdacklp |
| 17 | Cm | mglgktiqaiaisyyykkewpllivvpsslkypwidemekwipelcpddisiiqnktdigristskvtvlgy gllatdaqtlvdtlykqnfkivlvdeshymksrnatrskillpivqnaaraillltgtpalgrpeelfmqiealfprr fgtwneyakkycnahvrffgkrtlwdcrgasnldelhqllsnimirrlknevltqlppkirqripfdlpkaaa kelntsfeeweklmrapnsdvaeshfvqvmglitrmykqtaiakytrdkstserspvdsstppereaqaest gerqlltyrsedtragavkdyikmmlendklkflvfahhlsmlqacteaaienkaryiridgsvpsverihlv hqfqkdpdtrvailsiqaagqgltftaathvvfaelywdpghmkqaedrahrigqcssvnihyliakgtldpl mwamlnrkakvtgstlngkkeklqaeegdkekwdflsfaeawtpnesleevknevlfthfekekqhdir affspkpsaekkrkidswdkslnftsgdskvtpgkdieegsrhldareiidvdaicyengcepeakrpraist ptqssssekkrkilpgktntlftkesdhglsggslsnsrkksplakvwccslctytnnsllpyceicecprgsdd kqntnqmndppstlseeenasqdsrkikgiaicnadnerkdlvqtatessdeiggevanavengseeceqk pqegcvdnsdtfpvydvlnfcasrntdrihlytkdgkslncnfipldikldnwedlpesfqqkqnrslilrfvr ewssltamkqkiirksghtfcspilaaeeiskqqarlssatkryvtkedvavaslskanssggsvclvtkeaafy lkneqtsaqktdghstklllkdqkvspvlnadsvqaevvedpaiykgylqavdnkgnplclscqqptvhld qdcksiawetrfcslkcqedflirssqsylrskvfevehgvcqlcnlnaqelylsiknapknqrknllessvm sqlplgqlneiitnpaegqfwqvdhikpvysgggqcslenlqtlctvchkertakqakersqmkrrslasky gsditkffvkm |
| 18 | HCTV | mtkryqrkdwleqkyckesldkieiadicgvsrstvdywvdkhgvereykksdwlqekyweeelsage maemcevdrttilywmdchdierrgfsesselmwreneelreeqkerservfaespppviadgchleetk ekisesltgksnprwrggsseyyggrwdakrekailadseqcascgmtraehkqvygrdlhvhhkipvrv fddvsdahfevnlvtvcmecheefdrisrewqdrkmevpa |
| 19 | Cas12j19 | mpsykssrvlvrdvpeelvdhyershrvaaffmrlllamrrepyslrmrdgterevdldetddflrsagcee pdavsddlrsfalavlhqdnpkkrafIesencvsilcleksasgtryykrpgyqllkkaieeewgwdkfeasl ldertgevaekfaalsmedwrrffaardpddlgrellktdtregmaaalrlrergvfpvsvpehldldslkaa masaaerlkswlacnqravdekselrkrfeealdgvdpekyalfekfaaelqqadynvtkklvlavsakfp atepsefkrgveilkedgykplwedfrelgfvylaerkwerrrggaavtlcdaddspikvrfgltgrgrkfvls aagsrflitvklpcgdvgltavpsryfwnpsvgrttsnsfrieftkrttenrryvgevkeiglvrqrgryyffidy nfdpeevsdetkvgraffraplnesrpkpkdkltvmgidlginpafafavctlgecqdgirspvakmedvsf dstglrggigsqklhremhnlsdrcfygaryirlskklrdrgalndieaIrlleekyipgfrivhiedaderrrtvg rtvkeikqeykrirhqfylryhtskrdrtelisaeyfrmlflvknlrnllkswnryhwttgdrerrggnpdelks yvrryynnlrmdtlkkltcaivrtakehgatlvameniqrvdrddevkrrkenslslswapgmvlerveqelk negilawevdprhtsqtscitdefgyrslvakdtfyfeqdrkihridadvnaainiarrfltryrsltqlwaslld dgrylvnvtrqheraylelqtgapaatlnptaeasyelvglspeeeelaqtrikrkkrepfyrhegvwltrekh reqvhelrnqvlalgnakipeirt |
| 20 | Cas12j19 | atgcccagctacaagagcagcagagtgctggtgagggacgtgccagaggagctggtggaccactacgaaa gaagccacagggtggccgccttcttcatgagactgctgctggccatgagaagagagcccacagcctgagaa tgagggacggaaccgagagagaggtggacctggacgaaaccgacgacttcctgagaagcgccggatgcga ggagccagacgccgtgtctgacgacctgagaagcttcgccctggccgtgctgcaccaggacaacccaaaga agagagccttctggagagcgagaactgcgtgtcaatcctgtgtctggagaaaagcgcctccggcaccagata ctacaaaagacccggctaccagctgctgaagaaggccatcgaggaggagtgggagtggacaagttcgag gcctctctgctggacgagagaacaggagaagtggccgagaagttcgccgccctgagcatggaagactggag aagattcttcgccgccagagaccccgacgatctgggaagagagctgctgaagaccgacaccagagaaggca tggccgccgccctgagactgagagaaagaggagtgttccccgtgagcgtgcccgagcacctggacctggac agcctgaaggccgccatggccagcgccgctgaaagactgaagctggctggcctgtaaccagcgcgccgt ggacgagaagagcgaactgagaaagagattcgaggaggccctggacggagtggaccctgaaaagtgcc ctgtttgagaagttcgctgccgagctgcagcaggccgactacaacgtgaccaagaaactggtgctggccgtga gcgccaagttccccgctaccgagcctagcgagtttaagagggagtggagatcctgaaggaagatggctaca agccctgtgggaggactttagagagctgggcttcgtgtatctggccgagagaaagtgggaagaaagaagag gcggagccgccgtgaccctgtgtgacgctgacgacagccctatcaaggtgagatttggactgactggcagaa gcagaaagtttgtgctgtccgccgccgggagcagattcctgatcacagtgaagctgccctgcggcgatgtggg actgaccgccgtgcccagcaggtacttttggaaccctcagtgggcagaaccacctccaactcttttagaattga gttcaccaagcggaccaccgagaatcgcaggtacgtgggcgaggtgaaagagattggcctggtgaggcaga gaggcagatactatttttttcatcgactacaacttcgacccagaggaggtgagcgacgagacaaggtgggcag agccttcttcagagccccctgaacgagtcaagacctaagaactgaccgccgtgatggggattga cctgggcattaaccagcctttgcctttgccgtgtgccacctggccgaatgccaggacggaatccggagcccc gtggccaaatggaggacgtgagcttcgactctaccggactgagaggcggaatcggcagccagaagctgca cagagagatgcacaacctgagcgacagatgcttttacggcgccagatacattagactgagcaagaagctgag ggacagaggagctctgaacgatatcgaggctagactgctggaagagaagtacatccccggctttagaattgtg cacattgaggacgccgacgagagaagaagaaccgtgggaagaacagtgaaagaaatcaaacaggagtaca |

-continued

| SEQ ID No: | Sequence abbreviation | Sequence information |
|---|---|---|
| | | aaagaatcagacaccagttctacctgaggtaccacaccagcaagagggacagaacagagctgattagcgcc<br>gagtacttcagaatgctgttcctggtgaagaacctgagaaacctgctgaagagctggaacagataccactgga<br>caaccggcgacagagaaagaagaggagggaacccagacgagctgaagagctatgtgagatactataacaat<br>ctgagaatggacaccctgaagaaactgacctgcgccatcgtgaggaccgccaaggaacacggagccaccct<br>ggtggccatggagaacatccagagagtggacagggacgacgaggtgaaaagaagaaaggaaaatagcctg<br>ctgagcctgtgggcccccggaatggtgctggagagagtggagcaggagctgaagaacgagggaatcctgg<br>cctgggaggtggacccaagacatacaagtcagacaagctgcatcaccgacgaatttggctacagaagcctgg<br>tggccaaggacaccttctactttgaacaggacagaaaaatccacagaatcgacgccgacgtgaacgccgcca<br>tcaacatcgcccgccgcttcctgacccggtacaggagcctgacccagctgtgggccagcctgctggacgacg<br>gcagatacctggtgaacgtgaccagacagcacgagagagcctacctggaactgcagaceggcgccccgc<br>cgctacactgaaccctaccgccgaagccagctacgaactggtgggactgagccccgaagaagaagagctgg<br>cccagaccagaatcaaacgcaaaaagagagaaccattctacagacacgaaggcgtgtggctgacaagagag<br>aagcacagagagcaggtgcacgaactgagaaaccaggtgctggccctgggcaacgccaagatccccgaaa<br>tcagaacc |

DETAILED DESCRIPTION OF THE EMBODIMENTS

The following examples are only used to describe rather than limit the present disclosure. Unless otherwise specified, the experiments and methods described in the examples are basically conducted in accordance with conventional methods well known in the art and described in various references. For example, conventional techniques such as immunology, biochemistry, chemistry, molecular biology, microbiology, cell biology, genomics, and recombinant DNA used in the present disclosure can be found in "*MOLECULAR CLONING: A LABORATORY MANUAL*", Sambrook, Fritsch, and Maniatis, edition 2 (1989); "*CURRENT PROTOCOLS IN MOLECULAR BIOLOGY*" (edited by F. M. Ausubel et al., (1987)); and "*METHODS IN ENZYMOLOGY*" series (Academic Press Corporation): "*PCR 2: A PRACTICAL APPROACH* (edited by M. J. MacPherson, B. D. Hames, and G. R. Taylor (1995)), *ANTIBODIES, A LABORATORY MANUAL* edited by Harlow and Lane (1988), and "*ANIMAL CELL CULTURE*" (edited by R. I. Freshney (1987)).

In addition, if no specific conditions are specified in the examples, the examples will be conducted according to conventional conditions or the conditions recommended by the manufacturer. All of the used reagents or instruments which are not specified with manufacturers are conventional commercially-available products. Those skilled in the art know that the present disclosure is described by way of examples in the embodiments, and the examples are not intended to limit the protection scope of the present disclosure. All publications and other references mentioned herein are incorporated herein by reference in their entireties.

Example 1 Acquisition of an HNH Domain

Through bioinformatics analysis, HNH domains each with a nuclease cleavage activity derived from different species were acquired, and the following HNH domains were selected in this example:

| SEQ ID NO: | Source | Sequence abbreviation |
|---|---|---|
| 1 | Cas9 | Sa |
| 2 | Mycobacterium phage Severus | Mbps |
| 3 | Mycobacterium virus PMC | Mbvp |
| 4 | Arabidopsis thaliana | SNF2 |
| 5 | Papaver somniferum | Ps |

-continued

| SEQ ID NO: | Source | Sequence abbreviation |
|---|---|---|
| 6 | Glycine max | Gm |
| 7 | Chelonia mydas | Cm |
| 8 | Halovirus | HCTV |

Example 2 Design of Engineered Type V Cas Proteins and Verification of Editing Efficiencies of the Engineered Type V Cas Proteins In this example, Cas12i3 (which was called Cas12f4 in CN111757889B and called Cas12i3 in this example) was adopted as a parental type V Cas protein without an HNH domain. An amino acid sequence of WT Cas12i3 was shown in SEQ ID NO: 9.

In this example, an HNH domain derived from Cas9 (SEQ ID NO: 1) was inserted into different regions of a Cas protein shown in SEQ ID NO: 9 to obtain Cas12i3 proteins in which the HNH domain was fused different amino acid positions. Editing efficiencies of different Cas12i3 proteins were detected by the following method: A fluorescent reporter system for validation of Cas12i3 cleavage was constructed with reference to (Yang, Yi, et al. "Highly efficient and rapid detection of the cleavage activity of Cas9/gRNA via a fluorescent reporter." Applied biochemistry and biotechnology 180.4 (2016): 655-667.), where a fluorescent reporter vector carried a red fluorescent protein (RFP) and a non-luminous green fluorescent protein (GFFP), and a Cas vector carried a cyan fluorescent protein (CFP). A TTTTTTAACAGTGGCCTTATTAA (SEQ ID NO: 27) target on a GFFP sequence was selected for testing. 48 h after a Chinese hamster ovary (CHO) cell was transfected, a proportion of GFP fluorescence in CFP and RFP fluorescence was determined by flow cytometry (FCM) to determine an editing efficiency.

Editing efficiencies of WT Cas12i3 and Cas12i3 proteins in which the HNH domain was fused different amino acid positions were detected, and detection results were shown in FIG. 1. In FIG. 1, different dots represent editing efficiencies of different Cas proteins, and WT represents WT Cas12i3. It can be seen that most of the Cas12i3 proteins fused with the HNH domain have a lower editing efficiency than wild-type Cas12i3, but a Cas protein in which the HNH domain is fused at an N-terminus of Cas12i3 (N-HNH in FIG. 1) and a Cas protein in which the HNH domain is fused between amino acids 794 and 795 of Cas12i3 (795-HNH in FIG. 1) have a higher editing efficiency than WT Cas12i3.

N-HNH represents an engineered Cas protein obtained by inserting the HNH domain shown in SEQ ID NO: 1 between amino acids 1 and 2 from an N-terminus of SEQ ID NO: 9 (that is, an N-terminus of the HNH domain shown in SEQ ID NO: 1 is directly linked to the amino acid 1 of SEQ ID NO: 9, and a C-terminus of the HNH domain shown in SEQ ID NO: 1 is directly linked to the amino acid 2 of SEQ ID NO: 9). 795-HNH represents an engineered Cas protein obtained by inserting the HNH domain shown in SEQ ID NO: 1 between amino acids 794 and 795 from the N-terminus of SEQ ID NO: 9 (that is, the N-terminus of the HNH domain shown in SEQ ID NO: 1 is directly linked to the amino acid 794 of SEQ ID NO: 9, and the C-terminus of the HNH domain shown in SEQ ID NO: 1 is directly linked to the amino acid 795 of SEQ ID NO: 9).

In the previous research of the applicants, WT Cas12i3 is subjected to site-directed mutagenesis to obtain mutated Cas12i3 with an improved editing activity. For example, a Cas protein is obtained by mutating amino acids 7, 233, 267, 369, and 433 of WT Cas12i3 as recorded in a Chinese patent application (No. 2023100884374), and this Cas protein is defined as Cas12i-SF01 in the present disclosure (which is obtained by mutating amino acids 7, 233, 267, 369, and 433 of SEQ ID NO: 9 into R). For example, a Cas protein is obtained by mutating amino acids 165, 166, 267, and 854 of WT Cas12i3 as recorded in a Chinese patent application (No. 2023104503761), and this Cas protein is defined as D165R/D166R/D267R/A854R in the present disclosure (which is obtained by mutating amino acids 165, 166, 267, and 854 of SEQ ID NO: 9 into R).

Figure 2:
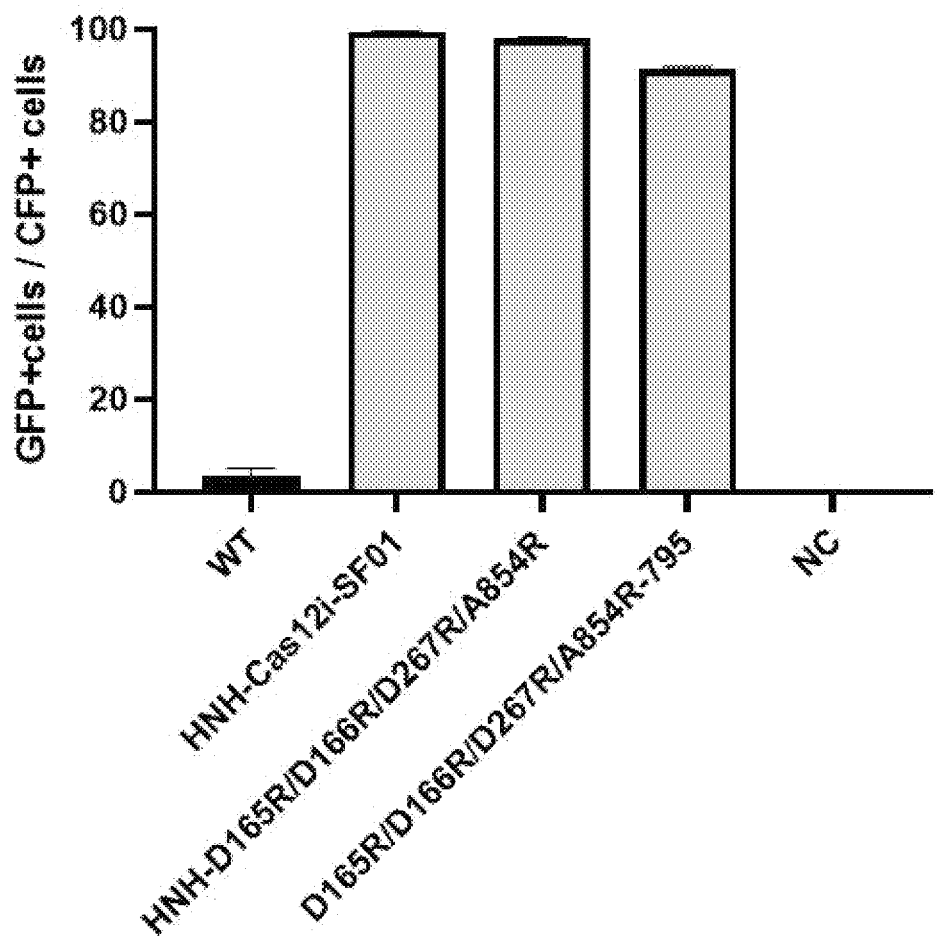
FIG. 2 shows detection results of an editing efficiency of mutated Cas12i3 in which an HNH domain is fused.

In order to verify an impact of the inserted HNH domain on the mutated Cas proteins Cas12i-SF01 and D165R/D166R/D267R/A854R, the applicants inserted the HNH domain shown in SEQ ID NO: 1 between amino acids 1 and 2 from an N-terminus of Cas12i-SF01 to obtain an engineered Cas protein HNH-Cas12i-SF01, inserted the HNH domain shown in SEQ ID NO: 1 between amino acids 1 and 2 from an N-terminus of D165R/D166R/D267R/A854R to obtain an engineered Cas protein HNH-D165R/D166R/D267R/A854R, and inserted the HNH domain shown in SEQ ID NO: 1 between amino acids 794 and 795 from an N-terminus of D165R/D166R/D267R/A854R to obtain an engineered Cas protein D165R/D166R/D267R/A854R-795. Editing efficiencies of HNH-Cas12i-SF01, HNH-D165R/D166R/D267R/A854R, and D165R/D166R/D267R/A854R-795 were detected by the above method, and detection results were shown in FIG. 2. It can be seen that the engineered Cas proteins with the HNH domain have a higher editing efficiency than the WT Cas12i3 (WT).

Figure 3:
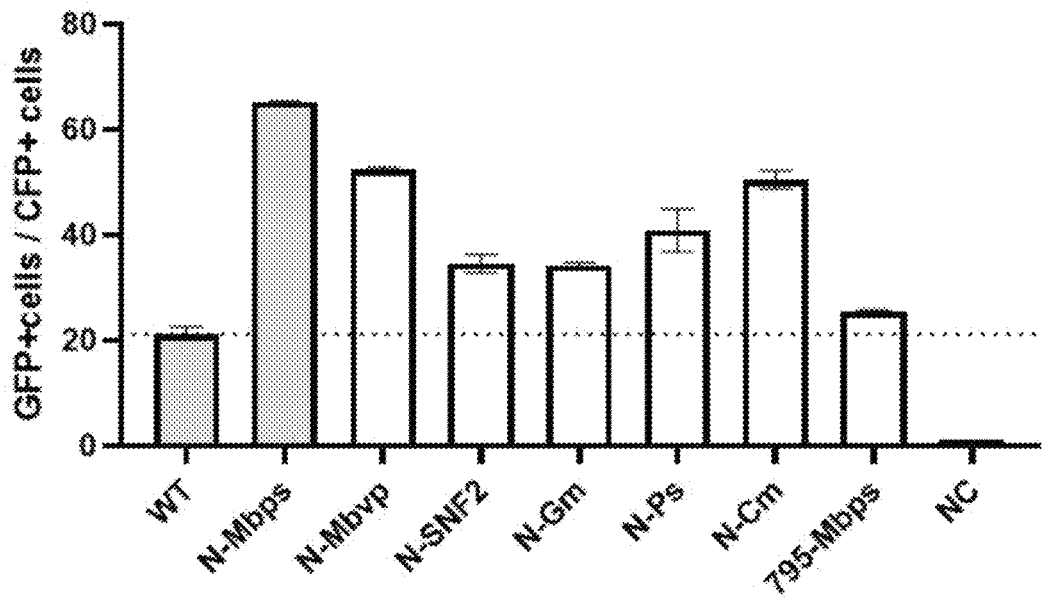
FIG. 3 shows an impact of fusion of different HNH domains on an editing efficiency of Cas12i3.

Example 3 Impacts of HNH Domains from Different Sources on an Activity of a Cas Protein The HNH domains from other sources recorded in Example 1 each were fused with Cas12i3 shown in SEQ ID NO: 9 to obtain different engineered Cas proteins. Specifically, the HNH domains shown in SEQ ID NOS: 2-7 each were inserted between amino acids 1 and 2 from an N-terminus of WT Cas12i3 to obtain engineered Cas proteins N-Mbps, N-Mbvp, N-SNF2, N-Ps, N-Gm, and N-Cm, respectively. The method in Example 2 was used to test an editing efficiency of the engineered Cas proteins, and test results were shown in FIG. 3. It can be seen that N-Mbps, N-Mbvp, N-SNF2, N-Ps, N-Gm, and N-Cm all have significantly-improved editing efficiencies compared with the WT Cas12i3 (WT), indicating that the insertion of any one of the HNH domains shown in SEQ ID NOS: 2-7 between amino acids 1 and 2 of Cas12i3 can improve an editing efficiency of a Cas protein, especially the N-Mbps protein in which the HNH domain shown in SEQ ID NO: 2 is inserted has a maximum editing efficiency.

To verify an impact of insertion of the HNH domain shown in SEQ ID NO: 2 at another position of SEQ ID NO: 9 on an editing efficiency of a Cas protein, the HNH domain shown in SEQ ID NO: 2 was inserted between amino acids 794 and 795 from an N-terminus of the WT Cas12i3 to obtain an engineered Cas protein 795-Mbps. An editing efficiency of the engineered Cas protein 795-Mbps was further detected by the above method, and detection results were shown in FIG. 3. It can be seen that 795-Mbps also has an improved editing efficiency compared with the WT Cas protein.

Example 4 Impact of an HNH Domain Inserted at N-Termini of Other Cas Proteins on an Activity of the Cas Proteins In this example, an HNH domain that was derived from Cas9 and shown in SEQ ID NO: 1 was inserted at N-termini of other type V Cas proteins. In this example, a type V Cas protein Cas12a (also known as Cpf1) was adopted, and specifically, the type V Cas protein was LbCas12a and had an amino acid sequence shown in SEQ ID NO: 10. In this example, another type V Cas protein Cas-sf0005 (recorded in a Chinese patent application CN114438055A) was also adopted, and WT Cas-sf0005 had an amino acid sequence shown in SEQ ID NO: 11. Mutated Cas-sf0005 used in this example was obtained by mutating amino acids 6, 149, 351, and 667 of the amino acid sequence (SEQ ID NO: 11) of the WT Cas-sf0005 into R, and was named Cas-05 E6R T149R T351R N667R.

An HNH domain shown in SEQ ID NO: 1 was inserted between amino acids 1 and 2 from an N-terminus of LbCas12a to obtain an engineered Cas protein HNH-Cas12a, and the HNH domain shown in SEQ ID NO: 1 was inserted between amino acids 1 and 2 from an N-terminus of Cas-05 E6R T149R T351R N667R to obtain an engineered Cas protein HNH-Cas05 E6R T149R T351R N667R.

Figure 4:
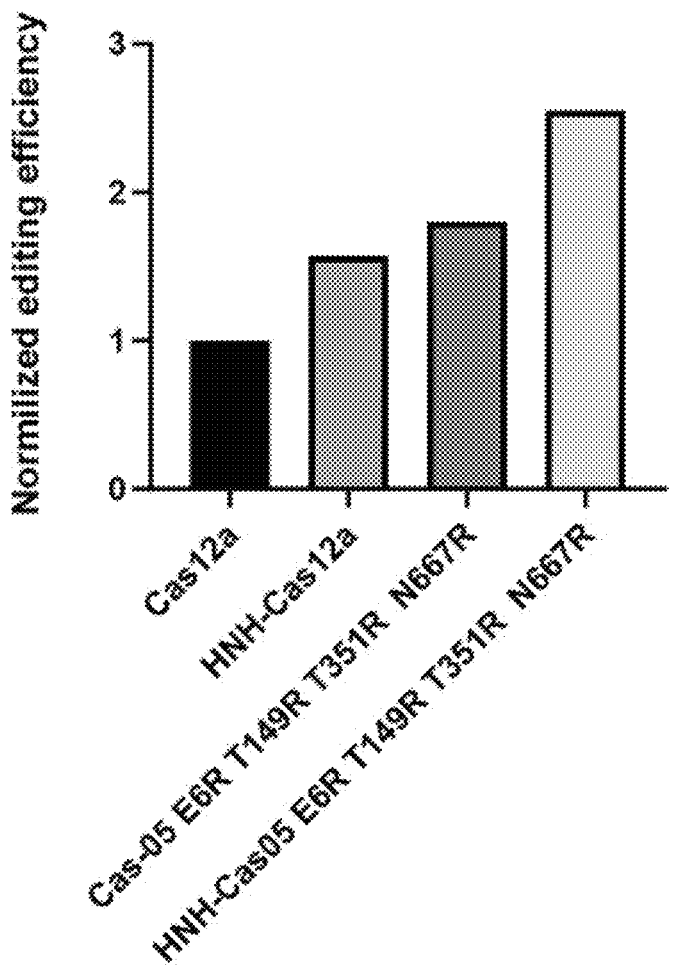
FIG. 4 shows an impact of fusion of an HNH domain on editing efficiencies of different type V Cas proteins.

Editing efficiencies of Cas12a, HNH-Cas12a, Cas-05 E6R T149R T351R N667R, and HNH-Cas05 E6R T149R T351R N667R were verified by a method similar to the method in Example 2, and verification results were shown in FIG. 4. It can be seen that the insertion of the HNH domain at N-termini of Cas12a and Cas-05 E6R T149R T351R N667R can significantly improve editing efficiencies of Cas12a and Cas-05 E6R T149R T351R N667R.

Example 5 Optimization of a Cas12J19 Protein

The applicants predicted possible key amino acid positions in the known Cas protein (which was called Cas12j.19 in CN111770992B and was called Cas12j19 in this example) to affect a biological function of the Cas protein through bioinformatics, and conducted a mutation at the amino acid positions to obtain mutated Cas proteins with improved editing activities. Specifically, a coding sequence for Cas12j19 was codon-optimized and synthesized. For WT Cas12j19, an amino acid sequence was shown in SEQ ID NO: 19 and a nucleic acid sequence was shown in SEQ ID NO: 20. Potential amino acids in Cas12j19 to bind to a target sequence were subjected to site-directed mutagenesis.

Variants of the Cas protein were produced through site-directed mutagenesis based on PCR. A specific method was as follows: A DNA sequence of the Cas12j19 protein was designed into two parts with a mutation site as a center, and two pairs of primers were designed to amplify the two parts of the DNA sequence, respectively; a sequence to be mutated was introduced into the primers; and finally, two amplified fragments were loaded on a pcDNA3.3-eGFP vector through Gibson cloning. A combination of mutants was constructed by splitting the DNA sequence of the Cas12j19 protein into a plurality of segments and then conducting PCR and Gibson cloning. A fragment amplification kit: TransStart FastPfu DNA Polymerase (including 2.5 mM dNTPs), a specific experimental procedure is detailed in the instructions. A gel recovery kit: FastPure® Gel DNA Extraction Mini Kit, a specific experimental procedure is detailed in the instructions. A kit for vector construction: pEASY-Basic Seamless Cloning and Assembly Kit (CU201-03), a specific experimental procedure is detailed in the instructions.

Based on the above amino acid mutation sites, WT Cas12j19 was obtained, and mutated proteins of Cas12j19 were obtained through a mutation at a single amino acid position or a combination of a plurality of different amino acid positions.

With reference to (Yang, Yi, et al. "Highly efficient and rapid detection of the cleavage activity of Cas9/gRNA via a fluorescent reporter." Applied biochemistry and biotechnology 180.4 (2016): 655-667.), a fluorescent reporter system for verification of Cas12j19 cleavage was constructed, where a fluorescent reporter vector carried an RFP and a non-luminous GFFP, and a Cas vector carried a CFP. A target FUT8-3: ATGGAGGCTGTCTACAATGGGGA (SEQ ID NO: 28) on a GFFP sequence was selected for testing, where an underlined part was a PAM sequence. A DR sequence was GUGCUGCUGUCUCCCAGACGG-GAGGCAGAACUGCAC (SEQ ID NO: 29). 48 h after a CHO cell was transfected, a proportion of GFP fluorescence in CFP and RFP fluorescence was determined by FCM to determine an editing efficiency.

Figure 5:
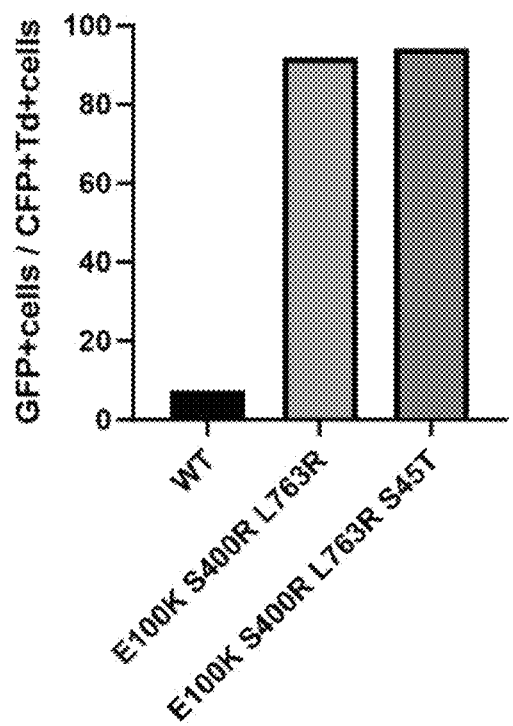
FIG. 5 shows verification results of an editing activity of a mutated Cas12j19 protein.

In this example, in SEQ ID NO: 19, an amino acid 100 was mutated into K, an amino acid 400 was mutated into R, and an amino acid 763 was mutated into R to obtain a three site-mutated protein E100K-S400R-L763R; and in SEQ ID NO: 19, an amino acid 100 was mutated into K, an amino acid 400 was mutated into R, an amino acid 763 was mutated into R, and an amino acid 45 was mutated into T to obtain a four site-mutated protein E100K-S400R-L763R-S45T. Activities of the different mutated proteins were tested by the above method, and test results were shown in FIG. 5. It can be seen that the WT Cas12j19 (SEQ ID NO: 19) has an editing efficiency of about 6%, and the three site-mutated protein E100K-S400R-L763R and the four site-mutated protein E100K-S400R-L763R-S45T both have an editing efficiency of about 90%, indicating that the editing efficiencies of the three site-mutated protein and the four site-mutated protein are significantly improved compared with the editing efficiency of the WT Cas12j19.

Example 6 Design of Engineered Type V Cas Proteins and Verification of Editing Efficiencies of the Engineered Type V Cas Proteins In this example, the four site-mutated protein E100K-S400R-L763R-S45T obtained in Example 5 was adopted as a parental protein, and an HNH domain was inserted into the parental protein. In this example, the four site-mutated protein E100K-S400R-L763R-S45T was defined as enCas-SF02.

In this example, an HNH domain (SEQ ID NO: 1) derived from Cas9 was inserted between amino acids 1 and 2 from an N-terminus of enCas-SF02 to obtain an engineered Cas protein SaHNH-enCas-SF02 in which the HNH domain was inserted (that is, an N-terminus of the HNH domain shown in SEQ ID NO: 1 was directly linked to the amino acid 1 of enCas-SF02, and a C-terminus of the HNH domain shown in SEQ ID NO: 1 was directly linked to the amino acid 2 of enCas-SF02).

In this example, an amino acid 100 in SEQ ID NO: 19 was mutated into K to obtain a single site-mutated protein Cas-SF02.

In this example, editing activities of the WT Cas12j19, the mutated proteins Cas-SF02 and enCas-SF02, and the engineered Cas protein SaHNH-enCas-SF02 were tested in a 293T cell.

For the 293T cell, the following test targets were designed, and PAMs all were ATG.

| Target name | Target sequence | |
|---|---|---|
| TTR-g1 | gcttctcatcgtctgctcct | (SEQ ID NO: 30) |
| TTR-g2 | agtggacttctgtgatggct | (SEQ ID NO: 31) |
| TTR-g3 | ctgtccgaggcagtcctgcc | (SEQ ID NO: 32) |
| TTR-g4 | tgttcagaaaggctgctgat | (SEQ ID NO: 33) |
| TTR-g5 | gctcccaggtgtcatcagca | (SEQ ID NO: 34) |
| TTR-g6 | ggctcacaactgaggaggaa | (SEQ ID NO: 35) |
| TTR-g7 | ccaagtgccttccagtaaga | (SEQ ID NO: 36) |
| TTR-g8 | agggacttctcctccagtgg | (SEQ ID NO: 37) |
| TTR-g9 | gaatactcttggttacatga | (SEQ ID NO: 38) |
| TTR-g10 | ttagaagtccaggcagagac | (SEQ ID NO: 39) |
| PCSK-g1 | ctctgggcaaagacagagga | (SEQ ID NO: 40) |
| PCSK-g2 | aataccagcccccggtaag | (SEQ ID NO: 41) |
| PCSK-g3 | acaggcacgagccccacagg | (SEQ ID NO: 42) |
| PCSK-g4 | cccagtttgaagtccagctc | (SEQ ID NO: 43) |
| PCSK-g5 | gaggagaggctgcctgtggg | (SEQ ID NO: 44) |
| PCSK-g6 | ggaggcactagcaggagtta | (SEQ ID NO: 45) |
| PCSK-g7 | cctctgcctaccttcctgtt | (SEQ ID NO: 46) |
| PCSK-g8 | tggtgggtccatgcaacatg | (SEQ ID NO: 47) |
| PCSK-g9 | tctgagttgctgccattgca | (SEQ ID NO: 48) |
| PCSK-g10 | tgtgctgacccggcctgggc | (SEQ ID NO: 49) |
| TRAC-g1 | tgtcacaaagtaaggattct | (SEQ ID NO: 50) |
| TRAC-g2 | tgtatatcacagacaaaact | (SEQ ID NO: 51) |
| TRAC-g3 | tcaagctggtcgagaaaagc | (SEQ ID NO: 52) |
| TRAC-g4 | acgctgcggctgtggtccag | (SEQ ID NO: 53) |
| TRAC-g5 | agcagattaaacccggccac | (SEQ ID NO: 54) |
| TRAC-g6 | cagaggaaggagcgagggag | (SEQ ID NO: 55) |

-continued

| Target name | Target sequence |
|---|---|
| TRAC-g7 | ccaccaactggatcctaccc (SEQ ID NO: 56) |
| TRAC-g8 | tcaggcagtgacaagcagca (SEQ ID NO: 57) |
| TRAC-99 | atggatcttcagtgggttct (SEQ ID NO: 58) |
| TRAC-g10 | ctgtgtatctgggcgtgttg (SEQ ID NO: 59) |

A vector pcDNA3.3 was modified to carry an enhanced green-fluorescent protein EGFP and a PuroR resistance gene. A fusion protein SV40 NLS-Cas-XX was inserted through cleavage sites XbaI and PstI, and a U6 promoter and a gRNA sequence were inserted through a cleavage site Mfe1. A CMV promoter was used to initiate the expression of a fusion protein SV40 NLS-Cas-XX-NLS-GFP. A protein Cas-XX-NLS was linked to GFP through a linker peptide T2A. A promoter EF-1α was used to initiate the expression of a puromycin resistance gene. Plating: 293T cells growing to a confluency of 70% to 80% were collected and inoculated into a 12-well plate at 8*10^4 cells/well. Transfection: 24 h after the plating, transfection was conducted as follows: 6.25 L of a Hieff Trans™ lipofection nucleic acid transfection reagent and 100 µL of opti-MEM were thoroughly mixed to obtain a diluted Hieff Trans™ lipofection nucleic acid transfection reagent. 2.5 µg of a plasmid and 100 µL of opti-MEM were thoroughly mixed to obtain a diluted plasmid. The diluted Hieff Trans™ lipofection nucleic acid transfection reagent was thoroughly mixed with the diluted plasmid to obtain a mixed solution, and the mixed solution was incubated at room temperature for 20 min and then added to the plate for transfection. 48 h after the transfection, cells were digested with trypsin-EDTA (0.05%), and cells with a GFP signal were sorted by fluorescence-activated cell sorting (FACS).

DNA was extracted, amplified by PCR, and sent for hiTOM sequencing: Cells were digested with trypsin, then collected, and subjected to gDNA extraction by a cell/tissue gDNA extraction kit (Bioteke). A region near a target on extracted gDNA was amplified. A PCR product was subjected to hiTOM sequencing. Sequencing data analysis: Types and proportions of sequences within a range of 15 nt upstream and 10 nt downstream of the target were counted, and sequences with a single-nucleotide variant (SNV) frequency of greater than or equal to 1% or a non-SNV mutation frequency of greater than or equal to 0.06% among the sequences were counted to obtain editing efficiencies of different Cas proteins for the target.

Figure 6:
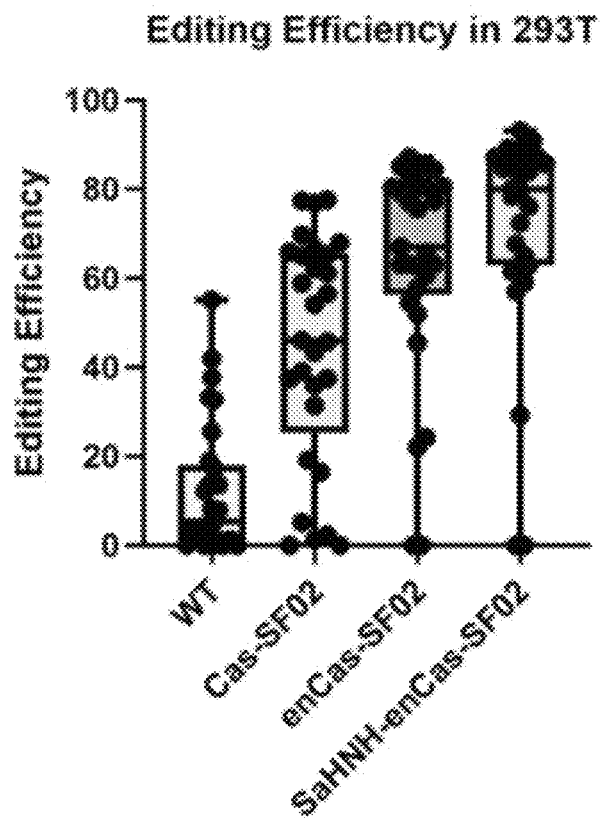
FIG. 6 shows verification results of an editing efficiency of engineered Cas12j19 in a 293T cell.

Editing efficiencies of the WT Cas12j19, the mutated proteins Cas-SF02 and enCas-SF02, and the engineered Cas protein SaHNH-enCas-SF02 at each target were counted, and results were shown in FIG. 6. It can be seen that the SaHNH-enCas-SF02 in which the HNH domain is inserted exhibits a greatly-improved editing efficiency in a eukaryotic cell compared with other proteins.

Example 7 Impacts of HNH Domains from Different Sources on an Activity of a Cas Protein In this example, different HNH domains (the HNH domains shown in SEQ ID NOS: 2-8 described in Example 1) were inserted between amino acids 1 and 2 from an N-terminus of the four site-mutated protein E100K-S400R-L763R-S45T of Cas12j19 to obtain engineered Cas proteins with different HNH domains: Mbps-enCas-SF02 (E100K-S400R-L763R-S45T in which the HNH domain shown in SEQ ID NO: 2 was inserted), Mbvp-enCas-SF02 (E100K-S400R-L763R-S45T in which the HNH domain shown in SEQ ID NO: 3 was inserted), SNF2-enCas-SF02 (E100K-S400R-L763R-S45T in which the HNH domain shown in SEQ ID NO: 4 was inserted), Ps-enCas-SF02 (E100K-S400R-L763R-S45T in which the HNH domain shown in SEQ ID NO: 5 was inserted), Gm-enCas-SF02 (E100K-S400R-L763R-S45T in which the HNH domain shown in SEQ ID NO: 6 was inserted), Cm-enCas-SF02 (E100K-S400R-L763R-S45T in which the HNH domain shown in SEQ ID NO: 7 was inserted), and HCTV-enCas-SF02 (E100K-S400R-L763R-S45T in which the HNH domain shown in SEQ ID NO: 8 was inserted).

Figure 7:
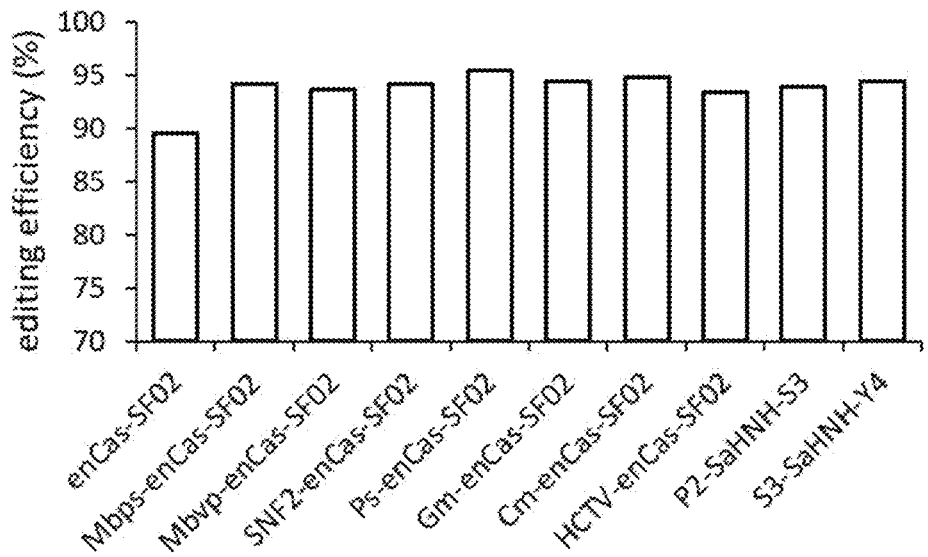
FIG. 7 shows an impact of fusion of different HNH domains on an editing efficiency of Cas12j19.

In addition, an HNH domain (shown in SEQ ID NO: 1) derived from Cas9 was inserted between amino acids 2 and 3 from an N-terminus of enCas-SF02 to obtain an engineered Cas protein P2-SaHNH-S3 in which the HNH domain was inserted; and the HNH domain (shown in SEQ ID NO: 1) derived from Cas9 was inserted between amino acids 3 and 4 from the N-terminus of enCas-SF02 to obtain an engineered Cas protein S3-SaHNH-Y4 in which the HNH domain was inserted, as shown in FIG. 7.

Editing activities of the Cas12j19 four site-mutated proteins E100K-S400R-L763R-S45T in which different HNH domains were fused were tested according to the method in Examples 5 and 6, and a test target was FUT8-3: ATG-GAGGCTGTCTACAATGGGGA (SEQ ID NO: 28). Test results were shown in FIG. 7. It can be seen that, compared with the Cas12j19 four site-mutated protein E100K-S400R-L763R-S45T (enCas-SF02 in FIG. 7), the Cas12j19 four site-mutated proteins E100K-S400R-L763R-S45T, P2-SaHNH-S3, and S3-SaHNH-Y4 in which different HNH domains were fused all exhibit a prominent editing activity.

Figure 8:
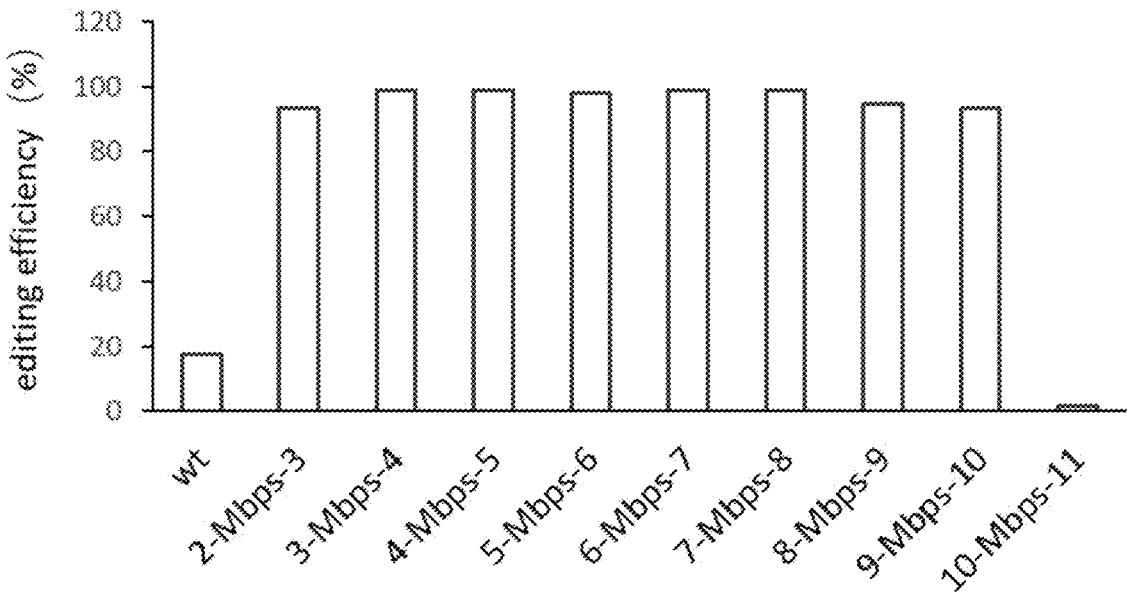
FIG. 8 shows an impact of an HNH domain inserted at different positions on an editing efficiency of Cas12i3.

Example 8 Impact of an HNH Domain Inserted at Different Amino Acid Positions from an N-Terminus of Cas12i3 on an Activity of the Protein In this example, an HNH domain shown in SEQ ID NO: 2 of Mbps was inserted to other positions at an N-terminus of Cas12i-SF01. Specifically, the HNH domain shown in SEQ ID NO: 2 of Mbps was inserted between amino acids 2 and 3, amino acids 3 and 4, amino acids 4 and 5, amino acids 5 and 6, amino acids 6 and 7, amino acids 7 and 8, amino acids 8 and 9, amino acids 9 and 10, and amino acids 10 and 11 from an N-terminus of Cas12i-SF01 to obtain different Cas12i-SF01 mutated proteins in which the HNH domain was fused, and editing efficiencies of the different mutated proteins were verified by the method in Example 2. Verification results were shown in FIG. 8. It can be seen that, compared with the WT Cas12i3, the insertion of the HNH domain shown in SEQ ID NO: 2 of Mbps between amino acids 2 and 3 (2-Mbps-3), amino acids 3 and 4 (3-Mbps-4), amino acids 4 and 5 (4-Mbps-5), amino acids 5 and 6 (5-Mbps-6), amino acids 6 and 7 (6-Mbps-7), amino acids 7 and 8 (7-Mbps-8), amino acids 8 and 9 (8-Mbps-9), or amino acids 9 and 10 (9-Mbps-10) from an N-terminus of Cas12i-SF01 can significantly improve an editing efficiency of the Cas protein, but the insertion of the HNH domain between amino acids 10 and 11 (10-Mbps-11) reduces an editing efficiency of the Cas protein.

Although the specific implementations of the present disclosure have been described in detail, those skilled in the art will understand that various modifications and changes can be made to the details according to all teachings published, and such modifications and changes all are within the protection scope of the present disclosure. The full content of the present disclosure is defined by the appended claims and any equivalents thereof.

What is claimed is:

1. An engineered type V Cas protein, consisting of a parental type V Cas protein and an HNH domain having nuclease cleavage activity, wherein the parental type V Cas protein comprises SEQ ID NO: 9, and wherein the HNH domain is located between amino acids 794 and 795 of SEQ ID NO: 9.

2. The engineered type V Cas protein according to claim 1, wherein the HNH domain is selected from one or more of an HNH domain derived from Cas9, an HNH domain derived from *Mycobacterium phage Severus* (Mbps), an HNH domain derived from *Mycobacterium* virus PMC (Mbvp), an HNH domain derived from *Arabidopsis thaliana*, an HNH domain derived from *Papaver somniferum*, an HNH domain derived from *Glycine max*, an HNH domain derived from *Chelonia mydas*, and an HNH domain derived from Halovirus.

3. The engineered type V Cas protein according to claim 1, wherein the HNH domain is selected from one or more of an amino acid sequence of SEQ ID NO: 1, an amino acid sequence of SEQ ID NO: 2, an amino acid sequence of SEQ ID NO: 3, an amino acid sequence of SEQ ID NO: 4, an amino acid sequence of SEQ ID NO: 5, an amino acid sequence of SEQ ID NO: 6, an amino acid sequence of SEQ ID NO: 7, and an amino acid sequence of SEQ ID NO: 8.

4. The engineered type V Cas protein according to claim 1, wherein any one or more of amino acids 7, 165, 166, 233, 235, 266, 267, 328, 369, 433, 559 and 854 of SEQ ID NO: 9 is mutated.

5. A CRISPR-Cas system comprising the engineered type V Cas protein according to claim 1 and at least one gRNA, wherein the at least one gRNA is configured to bind to the engineered type V Cas protein.

6. A fusion protein comprising the engineered type V Cas protein according to claim 1 and a modification part selected from the group consisting of a detectable marker, an epitope tag, a reporter gene sequence, a nuclear localization signal (NLS) sequence, a targeting moiety, a transcriptional activation domain, a transcriptional repression domain, a domain with nucleotide deaminase activity, a domain with demethylase activity, and a domain with histone modification activity.

7. A composition, comprising:
i) a protein component selected from the engineered type V Cas protein according to claim 1 or the fusion protein comprising the engineered type V Cas protein and the modification part according to claim 6; and (ii) a nucleic acid component, wherein the nucleic acid component is a gRNA configured for binding to the engineered type V Cas protein,
wherein the protein component and the nucleic acid component combine with each other to produce a complex.

8. An isolated activated CRISPR complex, comprising:
(i) a protein component selected from the engineered type V Cas protein according to claim 1 or the fusion protein comprising the engineered type V Cas protein and the modification part according to claim 6;
(ii) a nucleic acid component, wherein the nucleic acid component is a gRNA comprising a direct repeat configured for binding to the engineered type V Cas protein and a guide sequence configured for targeting a target sequence; and
(iii) the target sequence binding to the gRNA in (ii).

9. An isolated engineered host cell, comprising
the engineered type V Cas protein according to claim 1, or the fusion protein comprising the engineered type V Cas protein and the modification part according to claim 6, or
an isolated polynucleotide, wherein the isolated polynucleotide is a polynucleotide sequence encoding the engineered type V Cas protein or a polynucleotide sequence encoding the fusion protein, or
a vector comprising the isolated polynucleotide and a regulatory element operably linked to the isolated polynucleotide, or
a CRISPR-Cas system comprising the engineered type V Cas protein and at least one gRNA, wherein the at least one gRNA is configured to bind to the engineered type V Cas protein, or
a composition, wherein the composition comprises (i) a protein component selected from the engineered type V Cas protein or the fusion protein comprising the engineered type V Cas protein and the modification part; and (ii) a nucleic acid component, wherein the nucleic acid component is a gRNA configured for binding to the engineered type V Cas protein, wherein the protein component and the nucleic acid component combine with each other to produce a complex, or
an activated CRISPR complex, wherein the activated CRISPR complex comprises (i) a protein component selected from the engineered type V Cas protein or the fusion protein comprising the engineered type V Cas protein and the modification part; (ii) a nucleic acid component, wherein the nucleic acid component is a gRNA comprising a direct repeat configured for binding to the engineered type V Cas protein and a guide sequence configured for targeting a target sequence; and (iii) the target sequence binding to the gRNA in (ii).

10. A method of gene editing, gene targeting, or gene cleavage comprising contacting a cell with the engineered type V Cas protein according to claim 1, or the fusion protein comprising the engineered type V Cas protein and the modification part according to claim 6, or
an isolated polynucleotide, wherein the isolated polynucleotide is a polynucleotide sequence encoding the engineered type V Cas protein or a polynucleotide sequence encoding the fusion protein, or
a vector comprising the isolated polynucleotide and a regulatory element operably linked to the isolated polynucleotide, or
a CRISPR-Cas system comprising the engineered type V Cas protein and at least one gRNA wherein the at least one gRNA is configured to bind to the engineered type V Cas protein, and configured for binding the gene sequence, or
a composition, wherein the composition comprises (i) a protein component selected from the engineered type V Cas protein or the fusion protein comprising the engineered type V Cas protein and the modification part; and (ii) a nucleic acid component, wherein the nucleic acid component is a gRNA configured for binding to the engineered type V Cas protein, and configured for binding the gene sequence, wherein the protein component and the nucleic acid component combine with each other to produce a complex.

11. A method for editing a target nucleic acid, targeting the target nucleic acid, or cleaving the target nucleic acid, comprising: making the target nucleic acid in contact with the engineered type V Cas protein according to claim 1, or the fusion protein comprising the engineered type V Cas protein and the modification part according to claim 6, or
a CRISPR-Cas system comprising the engineered type V Cas protein and at least one gRNA, wherein the at least one gRNA is configured to bind to the engineered type V Cas protein, and configured for binding the target nucleic acid, or
a composition, wherein the composition comprises (i) a protein component selected from the engineered type V Cas protein or the fusion protein comprising the engineered type V Cas protein and the modification part; and (ii) a nucleic acid component, wherein the nucleic acid component is a gRNA configured for binding to the engineered type V Cas protein, and configured for binding the target nucleic acid wherein the protein component and the nucleic acid component combine with each other to produce a complex.

12. A kit for gene editing, gene targeting, or gene cleaving, comprising the engineered type V Cas protein according to claim 1, or the fusion protein comprising the engineered type V Cas protein and the modification part according to claim 6,
an isolated polynucleotide, wherein the isolated polynucleotide is a polynucleotide sequence encoding the engineered type V Cas protein or a polynucleotide sequence encoding the fusion protein, or
a vector comprising the isolated polynucleotide and a regulatory element operably linked to the isolated polynucleotide, or
a CRISPR-Cas system comprising the engineered type V Cas protein and at least one gRNA, wherein the at least gRNA is configured to bind to the engineered type V Cas protein and configured for binding the gene sequence or
a composition, wherein the composition comprises (i) a protein component selected from the engineered type V Cas protein or the fusion protein comprising the engineered type V Cas protein and a modification part; and (ii) a nucleic acid component, wherein the nucleic acid component is a gRNA configured for binding to the engineered type V Cas protein, and configured for binding the gene sequence, wherein the protein component and the nucleic acid component combine with each other to produce a complex.

13. A method of improving editing efficiency of a type V Cas protein comprising contacting a cell with an engineered type V Cas protein, consisting of a parental type V Cas protein and an HNH domain having nuclease cleavage activity, wherein the parental type V Cas protein comprises SEQ ID NO: 9, and wherein the HNH domain is located between amino acids 794 and 795 of SEQ ID NO: 9.

14. An isolated polynucleotide encoding an engineered type V Cas protein, consisting of a parental type V Cas protein and an HNH domain having nuclease cleavage activity, wherein the parental type V Cas protein comprises SEQ ID NO: 9, and wherein the HNH domain is located between amino acids 794 and 795 of SEQ ID NO: 9.

15. A vector comprising the isolated polynucleotide according to claim 14 and a regulatory element operably linked to the isolated polynucleotide.

* * * * *

SEQUENCE LISTING

```
Sequence total quantity: 65
SEQ ID NO: 1                moltype = AA   length = 109
FEATURE                     Location/Qualifiers
source                      1..109
                            mol_type = protein
                            organism = synthetic construct
SEQUENCE: 1
LIEKIKLHDM QEGKCLYSLE AIPLEDLLNN PFNYEVDHII PRSVSFDNSF NNKVLVKQEE    60
NSKKGNRTPF QYLSSSDSKI SYETFKKHIL NLAKGKGRIS KTKKEYLLE               109

SEQ ID NO: 2                moltype = AA   length = 33
FEATURE                     Location/Qualifiers
source                      1..33
                            mol_type = protein
                            organism = synthetic construct
SEQUENCE: 2
GKATDVDHIE RGDDHSRRNL QAACNRCHGK KSS                                 33

SEQ ID NO: 3                moltype = AA   length = 46
FEATURE                     Location/Qualifiers
source                      1..46
                            mol_type = protein
                            organism = synthetic construct
SEQUENCE: 3
CQSCGHTATP GSGQLHADHI QPRSRGGTDT LDNMRTLCKA CHAPKS                   46

SEQ ID NO: 4                moltype = AA   length = 33
FEATURE                     Location/Qualifiers
source                      1..33
                            mol_type = protein
                            organism = synthetic construct
SEQUENCE: 4
NAWHADHIIP VYQGGGECRL ENMRTLCVAC HAD                                 33

SEQ ID NO: 5                moltype = AA   length = 35
FEATURE                     Location/Qualifiers
source                      1..35
                            mol_type = protein
                            organism = synthetic construct
SEQUENCE: 5
NAWHADHIIP VYRGGGECNL DNMRTLCVAC HSDVT                               35

SEQ ID NO: 6                moltype = AA   length = 45
FEATURE                     Location/Qualifiers
source                      1..45
                            mol_type = protein
                            organism = synthetic construct
SEQUENCE: 6
CKRFFNCIGC LCYEYDHIIP FSKGGESTAD NCQILQSRVN RLKSD                    45

SEQ ID NO: 7                moltype = AA   length = 36
FEATURE                     Location/Qualifiers
source                      1..36
                            mol_type = protein
                            organism = synthetic construct
SEQUENCE: 7
QFWQVDHIKP VYSGGGQCSL ENLQTLCTVC HKERTA                              36

SEQ ID NO: 8                moltype = AA   length = 51
FEATURE                     Location/Qualifiers
source                      1..51
                            mol_type = protein
                            organism = synthetic construct
SEQUENCE: 8
CASCGMTRAE HKQVYGRDLH VHHKIPVRVF DDVSDAHFEV NLVTVCMECH E             51

SEQ ID NO: 9                moltype = AA   length = 1045
FEATURE                     Location/Qualifiers
source                      1..1045
                            mol_type = protein
                            organism = synthetic construct
SEQUENCE: 9
MKKVEVSRPY QSLLLPNHRK FKYLDETWNA YKSVKSLLHR FLVCAYGAVP FNKFVEVVEK    60
VDNDQLVLAF AVRLFRLVPV ESTSFAKVDK ANLAKSLANH LPVGTAIPAN VQSYFDSNFD   120
PKKYMWIDCA WEADRLAREM GLSASQFSEY ATTMLWEDWL PLNKDDVNGW GSVSGLFGEG   180
KKEDRQQKVK MLNNLLNGIK KNPPKDYTQY LKILLNAFDA KSHKEAVKNY KGDSTGRTAS   240
YLSEKSGEIT ELMLEQLMSN IQRDIGDKQK EISLPKKDVV KKYLESESGV PYDQNLWSQA   300
YRNAASSIKK TDTRNFNSTL EKFKNEVELR GLLSEGDDVE ILRSKFFSSE FHKTPDKFVI   360
```

```
KPEHIGFNNK YNVVAELYKL KAEATDFESA FATVKDEFEE KGIKHPIKNI LEYIWNNEVP   420
VEKWGRVARF NQSEEKLLRI KANPTVECNQ GMTFGNSAMV GEVLRSNYVS KKGALVSGEH   480
GGRLIGQNNM IWLEMRLLNK GKWETHHVPT HNMKFFEEVH AYNPSLADSV NVRNRLYRSE   540
DYTQLPSSIT DGLKGNPKAK LLKRQHCALN NMTANVLNPK LSFTINKKND DYTVIIVHSV   600
EVSKPRREVL VGDYLVGMDQ NQTASNTYAV MQVVKPKSTD AIPFRNMWVR FVESGSIESR   660
TLNSRGEYVD QLNHDGVDLF EIGDTEWVDS ARKFFNKLGV KHKDGTLVDL STAPRKAYAF   720
NNFYFKTMLN HLRSNEVDLT LLRNEILRVA NGRFSPMRLG SLSWTTLKAL GSFKSLVLSY   780
FDRLGAKEMV DKEAKDKSLF DLLVAINNKR SNKREERTSR IASSLMTVAQ KYKVDNAVVH   840
VVVEGNLSST DRSASKAHNR NTMDWCSRAV VKKLEDMCNL YGFNIKGVPA FYTSHQDPLV   900
HRADYDDPKP ALRCRYSSYS RADFSKWGQN ALAAVVRWAS NKKSNTCYKV GAVEFLKQHG   960
LFADKKLTVE QFLSKVKDEE ILIPRRGGRV FLTTHRLLAE STFVYLNGVK YHSCNADEVA  1020
AVNICLNDWV IPCKKKMKEE SSASG                                        1045

SEQ ID NO: 10            moltype = AA  length = 1228
FEATURE                  Location/Qualifiers
source                   1..1228
                         mol_type = protein
                         organism = synthetic construct
SEQUENCE: 10
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFDNREN MFSEEAKSTS IAFRCINENL   180
TRYISNMDIF EKVDAIFDKH EVQEIKEKIL NSDYDVEDFF EGEFFNFVLT QEGIDVYNAI   240
IGGFVTESGE KIKGLNEYIN LYNQKTKQKL PKFKPLYKQV LSDRESLSFY GEGYTSDEEV   300
LEVFRNTLNK NSEIFSSIKK LEKLFKNFDE YSSAGIFVKN GPAISTISKD IFGEWNVIRD   360
KWNAEYDDIH LKKKAVVTEK YEDDRRKSFK KIGSFSLEQL QEYADADLSV VEKLKEIIIQ   420
KVDEIYKVYG SSEKLFDADF VLEKSLKKND AVVAIMKDLL DSVKSFENYI KAFFGEGKET   480
NRDESFYGDF VLAYDILLKV DHIYDAIRNY VTQKPYSKDK FKLYFQNPQF MGGWDKDKET   540
DYRATILRYG SKYYLAIMDK KYAKCLQKID KDDVNGNYEK INYKLLPGPN KMLPKVFFSK   600
KWMAYYNPSE DIQKIYKNGT FKKGDMFNLN DCHKLIDFFK DSISRYPKWS NAYDFNFSET   660
EKYKDIAGFY REVEEQGYKV SFESASKKEV DKLVEEGKLY MFQIYNKDFS DKSHGTPNLH   720
TMYFKLLFDE NNHGQIRLSG GAELFMRRAS LKKEELVVHP ANSPIANKNP DNPKKTTTLS   780
YDVYKDKRFS EDQYELHIPI AINKCPKNIF KINTEVRVLL KHDDNPYVIG IDRGERNLLY   840
IVVVDGKGNI VEQYSLNEII NNFNGIRIKT DYHSLLDKKE KERFEARQNW TSIENIKELK   900
AGYISQVVHK ICELVEKYDA VIALEDLNSG FKNSRVKVEK QVYQKFEKML IDKLNYMVDK   960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                    1228

SEQ ID NO: 11            moltype = AA  length = 737
FEATURE                  Location/Qualifiers
source                   1..737
                         mol_type = protein
                         organism = synthetic construct
SEQUENCE: 11
MTPKTETPVG ALIKKFFPGK RFQKNYLKDA GKKLKREGEA AAVEYLSGKQ EDHPANFCPP    60
AKVNILAQSR PLSEWPINLV SKGVQEYVYG LTAAEREANG DFGTSRKSLD RWFARTGVPT   120
HGYTTVQGLN LILRHTFNRY DGVIKKVETR NEKRRSKATR INVSREADGL PPIEAEPEET   180
AFGPDGKLKE RPGINPSIYC YQQVSPVPYN PAKHPALPFS GVDPGAPLPL GTPNRLSIPK   240
GQPGYVPEWQ RPHLSTKNKR IRKWYARANW RRKPGRKSVL DEAKLKEAAL KEAIPIIVTI   300
GKDWIVMDAR GLLRAVYWRG IAKPGLSLKE LLGFFSGDPV LDPKRGIATF TFKLGAVAVH   360
SRKPTRGKKS KELLLSMTAE KPHVGLVAID LGQTNPVAAE FSRVKREGET LQAEPLGQIV   420
LPDDLVKDLT RYRRAWDATE EQIKAEAIVQ LPEECRASEV KVNQMSAEET KHLILDRGVS   480
GDLPWEKMTS NTTFISDHLL AKGVTDQVFF EKKSKGKKKG TETVKRKDYG WVKLLRPRLS   540
QETRKAVNDK TWELKRASTE YVRLSRRKTE LARRCVNYIV RETKRWTQCE DIAIVIEDLN   600
VRFFHGSGER PDGWDNFFIS KRENRWFIQV LHKAFSDLAL HRGLPVIEAN PARTSITCIR   660
CGHCDRNNRH GEMFLCLSCN DLRHADREIA TRNLTRVAVT GEMIPRRIEP GEQSGDTKKA   720
RSARKGKKAV ISKREAA                                                 737

SEQ ID NO: 12            moltype = AA  length = 98
FEATURE                  Location/Qualifiers
source                   1..98
                         mol_type = protein
                         organism = synthetic construct
SEQUENCE: 12
MSWSTSDRSS RLPADWEENY RQPVLRAAGY RCQIRQRGCL GKATDVDHIE RGDDHSRRNL    60
QAACNRCHGK KSSAEGHARK RQLRARRKRP AERHPGRQ                           98

SEQ ID NO: 13            moltype = AA  length = 108
FEATURE                  Location/Qualifiers
source                   1..108
                         mol_type = protein
                         organism = synthetic construct
SEQUENCE: 13
MPRAPKVCRH AGCTTLTTTG TCPQHTTHRW GNHQGRKVPH WLQRATFRRD NWTCQSCGHT    60
ATPGSGQLHA DHIQPRSRGG TDTLDNMRTL CKACHAPKSR AEARGSNT                108
```

-continued

```
SEQ ID NO: 14            moltype = AA   length = 1194
FEATURE                  Location/Qualifiers
source                   1..1194
                         mol_type = protein
                         organism = synthetic construct
SEQUENCE: 14
MEVSEEQRRR DEATRLAFAE KRKQSFDSSE NPQRQQDFRL AKCRKLDGSN DVCPQEGYRN    60
YEPVRVLSTS VPEKFRVRLE ICSPDSFSVT PVQLQGFRCP EEQECLRQLR KILSDAIPLH   120
YTQNDDGGKA GVYKIRDYNK VSGCLKRSKS VEVEGVPWKT LAVVEKLSQS YISGKWQPCL   180
PEHYTEEKVE QLIETLPRKL VNALLPFQLD GLRFGLRRGG RCFIADEMGL GKTLQAIAIA   240
GCFISEGSIL VVCPAVLRFT WAEELERWLP SCLPSDVHLV FGHQDNPAYL PRWPKVVVIS   300
YKMLQHLRTT MLEREWALLI VDESHHLRCS KKKSDPPEIK TVLDVAEKVK HIILLSGTPS   360
VSRPFDIFHQ INMLWPGLLG KDKYEFAKTY CEVGLVRGIQ GKIFQDFSKG TRLLELNILL   420
NQTVMIRRLK QHLLTQLPPK RRQIVTILLK KSDIALAMAI VSEAKKQKDG AIAEVTEKSH   480
EPDQNARGSN EAGHVNAENS DGPNSDKENQ LCGKLSYQQL GIAKLSAFRE WLSLHPLLSG   540
LDYTPEEIDG DRSSTKMVVF AHHHKVLDGI QEFICDKGIG FVRIDGTTLP RDRQLAVQSF   600
QFSSEVKIAI IGVEAGGVGL DFSAAQNVVF LELPKTPSLL LQAEDRAHRR GQTSAVNVYI   660
FCAKDTMDES NWQNLNKKLH RISSTTDGKY DGKTEIEIGG ASIFKPAEES SEREVLEGQP   720
SESNTVVADK IVESCDDPGT ETDVSNTIDL KDDMTSQLEI LEVCPFVENG SGSGMRSSGT   780
ISLTMLAQEN QENHKPKNLI ADDGLVKEVD SSSIFPLIDS LRFEVSQNTG RIHLYSCIPG   840
KDPRPRPHFQ NFRPEEIEAS NPSQGTTKEK NPESITDDPV HVLAILEFMK EWKSLRPIEK   900
RKLLGKPLQL PLSLELSYLS ESTSHNSEGL LRGGSKRRNT PFSEISIPLP ENAVWIKVNL   960
RSGHQRKEKE YTQAWSMSNE PLCKLCQKPC AGYNAKEPEY LEDLFCELAC YEDYRTRTSS  1020
RYIRQELFQI EHGICTNCKL DCHQLVKRLR PLPLEKRRTY INKAAPELFA RKNLLETLVN  1080
DPTEGNAWHA DHIIPVYQGG GECRLENMRT LCVACHADVT AAQCAERKLI RSKARKQLKN  1140
TLNELRNNPK QKDLSADENT KETDSATNEE EDELMIEVPG SAYSIDQKIN HDAS        1194

SEQ ID NO: 15            moltype = AA   length = 334
FEATURE                  Location/Qualifiers
source                   1..334
                         mol_type = protein
                         organism = synthetic construct
SEQUENCE: 15
MMENEAWQNI LQAFMKERNG LRPVDQKKLL RKPLQLPLTS ELWYLKESIN HGSEANDLMP    60
QGLLKGGSKQ RNTPLSEISQ PLPANASWKK ISLCRGRKKE KEYTQGWTVT GEPLCKLCQK   120
PCKGKLSKTP EYFEDLFCEM ACFQEYRVKT SQGSLREELF KMEHGVCVAC KLDCHELVNY   180
IRPLRYVARG REHVEKVAPN LARSKKLLDK LINYPREGNA WHADHIIPVY RGGGECNLDN   240
MRTLCVACHS DVTKAQSKER RLRNKRGKDR VRDILKGLKL GSSREHNSKE QDDIETRNKE   300
DEDDLLMIDV PGSDYSRATD TVTVSNQENQ DEAE                               334

SEQ ID NO: 16            moltype = AA   length = 162
FEATURE                  Location/Qualifiers
source                   1..162
                         mol_type = protein
                         organism = synthetic construct
SEQUENCE: 16
MSSSSPQRSR GDGEKRPRFF DSNAKAICWS KADTVPGRHP ERWRKDAAGN VVCKRFFNCI    60
GCLCYEYDHI IPFSKGGEST ADNCQILQSR VNRLKSDKYN IDSDQLKDYS CEVNFTDKEL   120
DIIEMAVYGD VMRPGNQCRC RTIAEKLGKF KPKDDTDACK LP                      162

SEQ ID NO: 17            moltype = AA   length = 1103
FEATURE                  Location/Qualifiers
source                   1..1103
                         mol_type = protein
                         organism = synthetic construct
SEQUENCE: 17
MGLGKTIQAI AISYYYKKEW PLLIVVPSSL KYPWIDEMEK WIPELCPDDI SIIQNKTDIG    60
RISTSKVTVL GYGLLATDAQ TLVDTLYKQN FKIVLVDESH YMKSRNATRS KILLPIVQNA   120
ARAILLTGTP ALGRPEELFM QIEALFPRRF GTWNEYAKY CNAHVRFFGK RTLWDCRGAS   180
NLDELHQLLS NIMIRRLKNE VLTQLPPKIR QRIPFDLPKA AAKELNTSFE EWEKLMRAPN   240
SDVAESHFVQ VMGLITRMYK QTAIAKYTRD KSTSERSPVD SSTPPEREAQ AESTGERQLL   300
TYRSEDTRAG AVKDYIKMML ENDKLKFLVF AHHLSMLQAC TEAAIENKAR YIRIDGSVPS   360
VERIHLVHQF QKDPDTRVAI LSIQAAGQGL TFTAATHVVF AELYWDPGHM KQAEDRAHRI   420
GQCSSVNIHY LIAKGTLDPL MWAMLNRKAK VTGSTLNGKK EKLQAEEGDK EKWDFLSFAE   480
AWTPNESLEE VKNEVLFTHF EKEKQHDIRA FFSPKPSAEK KRKIDSWDKS LNFTSGDSKV   540
TPGKDIEEGS RHLDAREIID VDAICYENGC EPEAKRPRAI STPTQSSSSE KKRKILPGKT   600
NTLFTKESDH GLSGGSLSNS RKKSPLAKVW CCSLCTYTNN SLLPYCEICE CPRGSDDKQN   660
TNQMNDPPST LSEEENASQD SRKIKGIAIC NADNERKDLV QTATESSDEI GGEVANAVEN   720
GSEECEQKPQ EGCVDNSDTF PVYDVLNFCA SRNTDRIHLY TKDGKSLNCN FIPLDIKLDN   780
WEDLPESFQQ KQNRSLILRF VREWSSLTAM KQKIIRKSGH TFCSPILAAE EISKQQARLS   840
STKRYVTKED VAVASLSKAN SSGGGVCLVT KEAAFYLKNE GTSAGKTDGH STKLLLKDGK   900
VSPVLNADSV QAEVVEDPAI YKGYLQAVDN KGNPLCLSCQ QPTVHLDQDC KSIAWETRFC   960
SLKCQEDFLI RSSQSYLRSK VFEVEHGVCQ LCNLNAQELY LSIKNAPKNQ RKNLLESSWM  1020
SQLPLGQLNE IITNPAEGQF WQVDHIKPVY SGGGQCSLEN LQTLCTVCHK ERTAKQAKER  1080
SQMKRRSLAS KYGSDITKFF VKM                                         1103

SEQ ID NO: 18            moltype = AA   length = 248
FEATURE                  Location/Qualifiers
source                   1..248
```

```
                          mol_type = protein
                          organism = synthetic construct
SEQUENCE: 18
MTKRYQRKDW LEQKYCKESL DKIEIADICG VSRSTVDYWV DKHGVEREYK KSDWLQEKYW    60
EEELSAGEMA EMCEVDRTTI LYWMDCHDIE RRGFSESSEL MWRENEELRE EQKERSERVF   120
AESPPPVIAD GCHLEETKEK ISESLTGKSN PRWRGGSSEY YGGRWDAKRE KAILADSEQC   180
ASCGMTRAEH KQVYGRDLHV HHKIPVRVFD DVSDAHFEVN LVTVCMECHE EFDRISREWQ   240
DRKMEVPA                                                            248

SEQ ID NO: 19             moltype = AA   length = 908
FEATURE                   Location/Qualifiers
source                    1..908
                          mol_type = protein
                          organism = synthetic construct
SEQUENCE: 19
MPSYKSSRVL VRDVPEELVD HYERSHRVAA FFMRLLLAMR REPYSLRMRD GTEREVDLDE    60
TDDFLRSAGC EEPDAVSDDL RSFALAVLHQ DNPKKRAFLE SENCVSILCL EKSASGTRYY   120
KRPGYQLLKK AIEEEWGWDK FEASLLDERT GEVAEKFAAL SMEDWRRFFA ARDPDDLGRE   180
LLKTDTREGM AAALRLRERG VFPVSVPEHL DLDSLKAAMA SAAERLKSWL ACNQRAVDEK   240
SELRKRFEEA LDGVDPEKYA LFEKFAAELQ QADYNVTKKL VLAVSAKFPA TEPSEFKRGV   300
EILKEDGYKP LWEDFRELGF VYLAERKWER RRGGAAVTLC DADDSPIKVR FGLTGRGRKF   360
VLSAAGSRFL ITVKLPCGDV GLTAVPSRYF WNPSVGRTTS NSFRIEFTKR TTENRRYVGE   420
VKEIGLVRQR GRYYFFIDYN FDPEEVSDET KVGRAFFRAP LNESRPKPKD KLTVMGIDLG   480
INPAFAFAVC TLGECQDGIR SPVAKMEDVS FDSTGLRGGI GSQKLHREMH NLSDRCFYGA   540
RYIRLSKKLR DRGALNDIEA RLLEEKYIPG FRIVHIEDAD ERRRTVGRTV KEIKQEYKRI   600
RHQFYLRYHT SKRDRTELIS AEYFRMLFLV KNLRNLLKSW NRYHWTTGDR ERRGGNPDEL   660
KSYVRYYNNL RMDTLKKLTC AIVRTAKEHG ATLVAMENIQ RVDRDDEVKR RKENSLLSLW   720
APGMVLERVE QELKNEGILA WEVDPRHTSQ TSCITDEFGY RSLVAKDTFY FEQDRKIHRI   780
DADVNAAINI ARRFLTRYRS LTQLWASLLD DGRYLVNVTR QHERAYLELQ TGAPAATLNP   840
TAEASYELVG LSPEEEELAQ TRIKRKKREP FYRHEGVWLT REKHREQVHE LRNQVLALGN   900
AKIPEIRT                                                            908

SEQ ID NO: 20             moltype = DNA   length = 2724
FEATURE                   Location/Qualifiers
source                    1..2724
                          mol_type = other DNA
                          organism = synthetic construct
SEQUENCE: 20
atgcccagct acaagagcag cagagtgctg gtgagggacg tgccagagga gctggtggac    60
cactacgaaa gaagccacag ggtggccgcc ttcttcatga actgctgct ggccatgaga   120
agagagccct acagcctgag aatgagggac ggaaccgaga gaggtgga cctggacgaa    180
accgacgact tcctgagaag cgccggatgc gaggagccaa cgccgtgtc tgacgacctg   240
agaagcttcg ccctggccgt gctgcaccag gacaacccaa agaagagagc cttctctggg   300
agcgagaact gcgtgtcaat cctgtgtctg gagaaaagcg cctccggcac cagatactac   360
aaaagacccg gctaccagct gctgaagaag gccatcgagg aggagtgggg atgggacaag   420
ttcgaggcct ctctgctgga cgagagaaca ggagaagtgg ccgagaagtt cgccgccctg   480
agcatggaag actggagaga attcttcgcc gccagagacc ccgacgatct gggaagagag   540
ctgctgaaga ccgacaccag agaaggcatg gccgccgccc tgagactgag agaaagagga   600
gtgttccccg tgagcgtgcc cgagcacctg gacctggaca gcctgaaggc cgccatggcc   660
agcgccgctg aaagactgaa gtcatggctg gcctgtaacc agcgcgccgt ggacgagaag   720
agcgaactga gaaagagatt cgaggaggcc ctggacggaa tggaccctga aaagtatgcc   780
ctgtttgaga agttcgctgc cgagctgcag caggccgact acaacgtgac caagaaactg   840
gtgctggccg tgagcgccaa gttccccgct accgagccta gcgagtttaa gagaggagtg   900
gagatcctga aggaagatgg ctacaagccc ctgtgggagg actttagaga gctgggcttt   960
gtgtatctgg ccgagagaaa gtgggaaaga agaagaggcg gagccgccgt gacccctgtt  1020
gacgctgacg acagccctat caaggtgaga tttggactga ctggcagagg cagaaagttt  1080
gtgctgtccg ccgccgggag cagattcctg atcacagtga agctgccctg cggcgatgtg  1140
ggactgaccg ccgtgcccag caggtacttt tggaacccct cagtgggcag aaccacctcc  1200
aactctttta gaattgagtt caccaagcgg accaccgaga atcgcagga cgtgggcgag  1260
gtgaaagaa ttggcctggt gaggcagaga ggcagatact attttttcat cgactacaac  1320
ttcgacccag aggaggtgag cgacgagacc aaggtgggca gagccttctt cagagccccc  1380
ctgaacgagt caagacctaa gccaaaggac aagctgaccg tgatggggat tgacctgggc  1440
attaacccag cctttgcctt tgccgtgtgc accctgggcg aatgccagga cggaatccgg  1500
agcccgtgg ccaaaatgga ggactgtgag ttcgactcta ccggactgag aggcggaatc  1560
ggcagccaga agctgcacag agagatgcac aacctgagcg acagatgctt ttacggcgcc  1620
agatacatta gactgagcaa gaagctgagg gacagaggag ctctgaacga tatcgaggct  1680
agactgctgg aagagaagta catccccggc tttagaattg tgcacattga ggacgccgac  1740
gagagaagaa gaaccgtggg aagaacagtg aaagaaatca aacaggagta caaaagaatc  1800
agacaccagt tctacctgag gtaccacacc agcaagaggg acagacagga gctgattagc  1860
gccgagtact tcagaatgct gttcctggtg aagaacctga aaacctgct gaagagctgg  1920
aacagatacc actggacaac cggcgacaga gaaagaagag agggaaccc agcgagctg  1980
aagagctatg tgagatacta taacaatctg agaatggaca ccctgaagaa actgacctgc  2040
gccatcgtga ggaccgccaa ggaacacgga gccaccctga tggccatgga aaacatccag  2100
agagtggacg agggacgaga ggtgaaaaga agaaagaaat atgcctgt gagcctgtgg  2160
gcccccggaa tggtgctgga gagagtggag caggagctga gaacgaggg aatcctggcc  2220
tgggaggtgg acccaagaca tacaagtcag acaagctgca tcaccgacga atttggctac  2280
agaagcctgg tggccaagga caccttctac tttgaacagg acagaaaaat ccacagaatc  2340
gacgccgacg tgaacgccgc catcaacatc gcccgccgct tcctgacccg gtacaggagc  2400
ctgacccagc tgtgggccag cctgctggac gacggcagat acctggtgaa cgtgaccaga  2460
```

```
cagcacgaga gagcctacct ggaactgcag accggcgccc ccgccgctac actgaaccct    2520
accgccgaag ccagctacga actggtggga ctgagccccg aagaagaaga gctggcccag    2580
accagaatca aacgcaaaaa gagagaacca ttctacagac acgaaggcgt gtggctgaca    2640
agagagaagc acagagagca ggtgcacgaa ctgagaaacc aggtgctggc cctgggcaac    2700
gccaagatcc ccgaaatcag aacc                                            2724
```

```
SEQ ID NO: 21          moltype = AA   length = 7
FEATURE                Location/Qualifiers
source                 1..7
                       mol_type = protein
                       organism = synthetic construct
SEQUENCE: 21
PKKKRKV                                                                  7

SEQ ID NO: 22          moltype = AA   length = 20
FEATURE                Location/Qualifiers
source                 1..20
                       mol_type = protein
                       organism = synthetic construct
SEQUENCE: 22
AVKRPAATKK AGQAKKKKLD                                                   20

SEQ ID NO: 23          moltype = AA   length = 9
FEATURE                Location/Qualifiers
source                 1..9
                       mol_type = protein
                       organism = synthetic construct
SEQUENCE: 23
PAAKRVKLD                                                                9

SEQ ID NO: 24          moltype = AA   length = 25
FEATURE                Location/Qualifiers
source                 1..25
                       mol_type = protein
                       organism = synthetic construct
SEQUENCE: 24
MSRRRKANPT KLSENAKKLA KEVEN                                             25

SEQ ID NO: 25          moltype = AA   length = 9
FEATURE                Location/Qualifiers
source                 1..9
                       mol_type = protein
                       organism = synthetic construct
SEQUENCE: 25
KLKIKRPVK                                                                9

SEQ ID NO: 26          moltype = AA   length = 5
FEATURE                Location/Qualifiers
source                 1..5
                       mol_type = protein
                       organism = synthetic construct
SEQUENCE: 26
KIPIK                                                                    5

SEQ ID NO: 27          moltype = DNA  length = 23
FEATURE                Location/Qualifiers
source                 1..23
                       mol_type = other DNA
                       organism = synthetic construct
SEQUENCE: 27
tttttaaca gtggccttat taa                                                23

SEQ ID NO: 28          moltype = DNA  length = 23
FEATURE                Location/Qualifiers
source                 1..23
                       mol_type = other DNA
                       organism = synthetic construct
SEQUENCE: 28
atggaggctg tctacaatgg gga                                               23

SEQ ID NO: 29          moltype = RNA  length = 36
FEATURE                Location/Qualifiers
source                 1..36
                       mol_type = other RNA
                       organism = synthetic construct
SEQUENCE: 29
gtgctgctgt ctcccagacg ggaggcagaa ctgcac                                 36

SEQ ID NO: 30          moltype = DNA  length = 20
```

```
FEATURE                 Location/Qualifiers
source                  1..20
                        mol_type = other DNA
                        organism = synthetic construct
SEQUENCE: 30
gcttctcatc gtctgctcct                                              20

SEQ ID NO: 31           moltype = DNA   length = 20
FEATURE                 Location/Qualifiers
source                  1..20
                        mol_type = other DNA
                        organism = synthetic construct
SEQUENCE: 31
agtggacttc tgtgatggct                                              20

SEQ ID NO: 32           moltype = DNA   length = 20
FEATURE                 Location/Qualifiers
source                  1..20
                        mol_type = other DNA
                        organism = synthetic construct
SEQUENCE: 32
ctgtccgagg cagtcctgcc                                              20

SEQ ID NO: 33           moltype = DNA   length = 20
FEATURE                 Location/Qualifiers
source                  1..20
                        mol_type = other DNA
                        organism = synthetic construct
SEQUENCE: 33
tgttcagaaa ggctgctgat                                              20

SEQ ID NO: 34           moltype = DNA   length = 20
FEATURE                 Location/Qualifiers
source                  1..20
                        mol_type = other DNA
                        organism = synthetic construct
SEQUENCE: 34
gctcccaggt gtcatcagca                                              20

SEQ ID NO: 35           moltype = DNA   length = 20
FEATURE                 Location/Qualifiers
source                  1..20
                        mol_type = other DNA
                        organism = synthetic construct
SEQUENCE: 35
ggctcacaac tgaggaggaa                                              20

SEQ ID NO: 36           moltype = DNA   length = 20
FEATURE                 Location/Qualifiers
source                  1..20
                        mol_type = other DNA
                        organism = synthetic construct
SEQUENCE: 36
ccaagtgcct tccagtaaga                                              20

SEQ ID NO: 37           moltype = DNA   length = 20
FEATURE                 Location/Qualifiers
source                  1..20
                        mol_type = other DNA
                        organism = synthetic construct
SEQUENCE: 37
agggacttct cctccagtgg                                              20

SEQ ID NO: 38           moltype = DNA   length = 20
FEATURE                 Location/Qualifiers
source                  1..20
                        mol_type = other DNA
                        organism = synthetic construct
SEQUENCE: 38
gaatactctt ggttacatga                                              20

SEQ ID NO: 39           moltype = DNA   length = 20
FEATURE                 Location/Qualifiers
source                  1..20
                        mol_type = other DNA
                        organism = synthetic construct
SEQUENCE: 39
ttagaagtcc aggcagagac                                              20
```

```
SEQ ID NO: 40           moltype = DNA   length = 20
FEATURE                 Location/Qualifiers
source                  1..20
                        mol_type = other DNA
                        organism = synthetic construct
SEQUENCE: 40
ctctgggcaa agacagagga                                                     20

SEQ ID NO: 41           moltype = DNA   length = 20
FEATURE                 Location/Qualifiers
source                  1..20
                        mol_type = other DNA
                        organism = synthetic construct
SEQUENCE: 41
aataccagcc ccccggtaag                                                     20

SEQ ID NO: 42           moltype = DNA   length = 20
FEATURE                 Location/Qualifiers
source                  1..20
                        mol_type = other DNA
                        organism = synthetic construct
SEQUENCE: 42
acaggcacga gccccacagg                                                     20

SEQ ID NO: 43           moltype = DNA   length = 20
FEATURE                 Location/Qualifiers
source                  1..20
                        mol_type = other DNA
                        organism = synthetic construct
SEQUENCE: 43
cccagtttga agtccagctc                                                     20

SEQ ID NO: 44           moltype = DNA   length = 20
FEATURE                 Location/Qualifiers
source                  1..20
                        mol_type = other DNA
                        organism = synthetic construct
SEQUENCE: 44
gaggagaggc tgcctgtggg                                                     20

SEQ ID NO: 45           moltype = DNA   length = 20
FEATURE                 Location/Qualifiers
source                  1..20
                        mol_type = other DNA
                        organism = synthetic construct
SEQUENCE: 45
ggaggcacta gcaggagtta                                                     20

SEQ ID NO: 46           moltype = DNA   length = 20
FEATURE                 Location/Qualifiers
source                  1..20
                        mol_type = other DNA
                        organism = synthetic construct
SEQUENCE: 46
cctctgccta ccttcctgtt                                                     20

SEQ ID NO: 47           moltype = DNA   length = 20
FEATURE                 Location/Qualifiers
source                  1..20
                        mol_type = other DNA
                        organism = synthetic construct
SEQUENCE: 47
tggtgggtcc atgcaacatg                                                     20

SEQ ID NO: 48           moltype = DNA   length = 20
FEATURE                 Location/Qualifiers
source                  1..20
                        mol_type = other DNA
                        organism = synthetic construct
SEQUENCE: 48
tctgagttgc tgccattgca                                                     20

SEQ ID NO: 49           moltype = DNA   length = 20
FEATURE                 Location/Qualifiers
source                  1..20
                        mol_type = other DNA
                        organism = synthetic construct
SEQUENCE: 49
tgtgctgacc cggcctgggc                                                     20
```

| | | |
|---|---|---|
| SEQ ID NO: 50<br>FEATURE<br>source | moltype = DNA length = 20<br>Location/Qualifiers<br>1..20<br>mol_type = other DNA<br>organism = synthetic construct | |
| SEQUENCE: 50<br>tgtcacaaag taaggattct | | 20 |
| SEQ ID NO: 51<br>FEATURE<br>source | moltype = DNA length = 20<br>Location/Qualifiers<br>1..20<br>mol_type = other DNA<br>organism = synthetic construct | |
| SEQUENCE: 51<br>tgtatatcac agacaaaact | | 20 |
| SEQ ID NO: 52<br>FEATURE<br>source | moltype = DNA length = 20<br>Location/Qualifiers<br>1..20<br>mol_type = other DNA<br>organism = synthetic construct | |
| SEQUENCE: 52<br>tcaagctggt cgagaaaagc | | 20 |
| SEQ ID NO: 53<br>FEATURE<br>source | moltype = DNA length = 20<br>Location/Qualifiers<br>1..20<br>mol_type = other DNA<br>organism = synthetic construct | |
| SEQUENCE: 53<br>acgctgcggc tgtggtccag | | 20 |
| SEQ ID NO: 54<br>FEATURE<br>source | moltype = DNA length = 20<br>Location/Qualifiers<br>1..20<br>mol_type = other DNA<br>organism = synthetic construct | |
| SEQUENCE: 54<br>agcagattaa acccggccac | | 20 |
| SEQ ID NO: 55<br>FEATURE<br>source | moltype = DNA length = 20<br>Location/Qualifiers<br>1..20<br>mol_type = other DNA<br>organism = synthetic construct | |
| SEQUENCE: 55<br>cagaggaagg agcgagggag | | 20 |
| SEQ ID NO: 56<br>FEATURE<br>source | moltype = DNA length = 20<br>Location/Qualifiers<br>1..20<br>mol_type = other DNA<br>organism = synthetic construct | |
| SEQUENCE: 56<br>ccaccaactg gatcctaccc | | 20 |
| SEQ ID NO: 57<br>FEATURE<br>source | moltype = DNA length = 20<br>Location/Qualifiers<br>1..20<br>mol_type = other DNA<br>organism = synthetic construct | |
| SEQUENCE: 57<br>tcaggcagtg acaagcagca | | 20 |
| SEQ ID NO: 58<br>FEATURE<br>source | moltype = DNA length = 20<br>Location/Qualifiers<br>1..20<br>mol_type = other DNA<br>organism = synthetic construct | |
| SEQUENCE: 58<br>atggatcttc agtgggttct | | 20 |
| SEQ ID NO: 59<br>FEATURE<br>source | moltype = DNA length = 20<br>Location/Qualifiers<br>1..20<br>mol_type = other DNA<br>organism = synthetic construct | |
| SEQUENCE: 59 | | |

```
ctgtgtatct gggcgtgttg                                                    20

SEQ ID NO: 60           moltype = AA  length = 4
FEATURE                 Location/Qualifiers
source                  1..4
                        mol_type = protein
                        organism = synthetic construct
SEQUENCE: 60
GSSG                                                                      4

SEQ ID NO: 61           moltype = AA  length = 4
FEATURE                 Location/Qualifiers
source                  1..4
                        mol_type = protein
                        organism = synthetic construct
SEQUENCE: 61
SGGS                                                                      4

SEQ ID NO: 62           moltype = AA  length = 5
FEATURE                 Location/Qualifiers
source                  1..5
                        mol_type = protein
                        organism = synthetic construct
SEQUENCE: 62
GGGGS                                                                     5

SEQ ID NO: 63           moltype = AA  length = 10
FEATURE                 Location/Qualifiers
source                  1..10
                        mol_type = protein
                        organism = synthetic construct
SEQUENCE: 63
SGGSGGSGGS                                                               10

SEQ ID NO: 64           moltype = AA  length = 16
FEATURE                 Location/Qualifiers
source                  1..16
                        mol_type = protein
                        organism = synthetic construct
SEQUENCE: 64
SGSETPGTSE SATPES                                                        16

SEQ ID NO: 65           moltype = AA  length = 32
FEATURE                 Location/Qualifiers
source                  1..32
                        mol_type = protein
                        organism = synthetic construct
SEQUENCE: 65
SGGSSGGSSG SETPGTSESA TPESSGGSSG GS                                      32
```